United States Patent [19]

Dillard et al.

[11] Patent Number: 5,552,441
[45] Date of Patent: Sep. 3, 1996

[54] LEUKOTRIENE B4 ANTAGONISTS

[75] Inventors: Robert D. Dillard, Zionsville; J. Scott Sawyer, Indianapolis; Michael J. Sofia, Carmel, all of Ind.

[73] Assignee: Eli Lilly and Company, Indianapolis, Ind.

[21] Appl. No.: 195,951

[22] Filed: Feb. 14, 1994

Related U.S. Application Data

[62] Division of Ser. No. 988,615, Dec. 10, 1992, Pat. No. 5,324,743.
[51] Int. Cl.$^6$ .............................. A61K 31/19; C07C 63/04
[52] U.S. Cl. ........................ 514/569; 514/571; 562/461; 562/464
[58] Field of Search .................................. 562/461, 464; 514/569, 571

[56] References Cited

U.S. PATENT DOCUMENTS

| | | |
|---|---|---|
| 4,200,577 | 4/1980 | Buckle et al. . |
| 4,211,791 | 7/1980 | Buckle et al. . |
| 4,945,099 | 7/1990 | Bollinger et al. . |

OTHER PUBLICATIONS

Buckle et al., J. Med. Chem 22 (2) 158–68 (1979).

*Primary Examiner*—Johann Richter
*Assistant Examiner*—John Peabody
*Attorney, Agent, or Firm*—Roger S. Benjamin; David E. Boone

[57] ABSTRACT

This invention provides certain 1,2,4,5 substituted benzene derivatives containing "acid" substituents derived from cyclic or heterocyclic moieties. These unique compounds are leukotriene $B_4$ antagonists and formulations of these derivatives, and a method of using these derivatives for the treatment of conditions characterized by an excessive release of leukotrienes.

14 Claims, No Drawings

LEUKOTRIENE B4 ANTAGONISTS

This application is a division of prior application Ser. No. 07/988,615, filed Dec. 10, 1992, now U.S. Pat. No. 5,324,743.

Research in the area of allergic reactions of the lung provided evidence that arachidonic acid derivatives formed by the action of lipoxygenases are related to various disease states. These arachidonic acid metabolites have been classified as members of a family of eicosatetraenoic acids termed leukotrienes. Three of these substances, leukotriene $C_4$, leukotriene $D_4$, and leukotriene $E_4$ are believed to be major components of what has previously been referred to as slow reacting substance of anaphylaxis (SRS-A). Another, leukotiene, referred to as $LTB_4$, is a proinflammatory lipid implicated in the pathogenesis of psoriasis, arthritis, chronic lung diseases, inflammatory bowel diseases and other inflammatory states. This leukotriene $B_4$ ($LTB_4$) appears also to be present in other diseases such as endotoxic shock, septic shock, and adult respiratory distress syndrome. These diseases are characterized by the infiltration and aggregation of polymorphonuclear leukocytes, which when aggregated liberate tissue degrading enzymes and reactive chemicals causing the inflammation and severe disease states. Antagonism of $LTB_4$ should therefore provide a novel therapeutic approach to treating these conditions.

It is therefore an object of this invention to provide novel chemical agents which can be used in the treatment of inflammation, which agents antagonize $LTB_4$ and should be useful in treating conditions such as asthma, psoraisis, arthritis, chronic lung diseases, inflammatory bowel disease, endotoxic and septic shock, and adult respiratory distress syndrome.

SUMMARY OF THE INVENTION

This invention provides compounds having the structural formula:

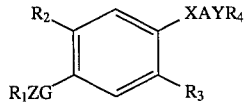

and salts thereof, wherein:

$R_1$ is hydrogen;

$R_2$ is halo, or —OR";

$R_3$ is $C_1$-$C_{10}$ alkyl, $C_1$-$C_6$ alkanoyl, $C_2$-$C_6$ alkenyl, $C_2$-$C_6$ alkynyl, $C_1$-$C_4$ alkoxy, hydroxy substituted $C_1$-$C_3$ alkyl, or $C_1$-$C_4$ thioalkyl;

X and Y may be the same or different groups individually selected, at each occurrence, from —CR'$_2$—, —O—, —S—, or —NR'"—;

Z is —(CH$_2$—)$_n$ or phenylene or —NR'"—;

A is a bond or a straight or branched chain $C_1$-$C_{10}$ alkylidene;

G is

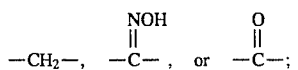

and
wherein:
each R' is independently hydrogen or $C_{1-4}$ alkyl;
each R" is independently H or —(CH$_2$—)$_n$H;
each R'" is independently H or $C_1$-$C_4$ alkyl;

n is selected individually at each occurrence and ranges from 1–8;

m is selected individually at each occurrence and ranges from 0–4; and
wherein
$R_4$ is selected from the groups;

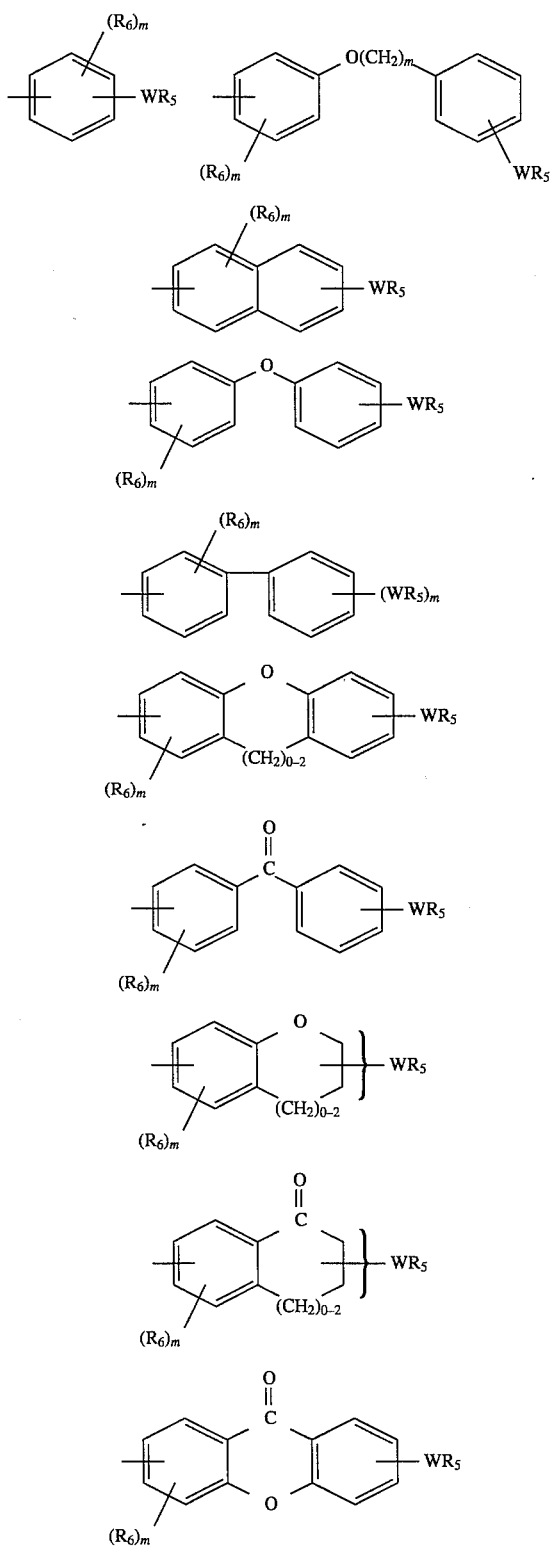

-continued

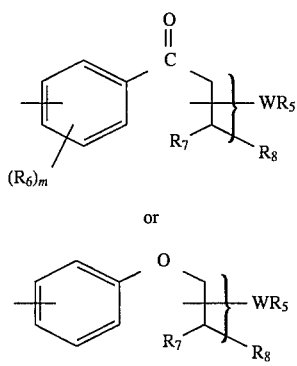

or

wherein

W is a bond, —(CHR')$_n$—, —(O[CHR']$_n$)$_n$—, —O—, —S—, or

and $R_5$ is H, $C_1$-$C_6$ linear or branched alkyl, $C_2$-$C_6$ alkenyl, $C_2$-$C_6$ alkynyl, hydroxy, 1,2,4-triazol-1-yl, —CN, halo, —$N_3$, —NR'R'", —$CO_2$R', or 5-tetrazolyl optionally substituted with a $C_1$-$C_4$ alkyl group; and $R_6$ is individually selected at each occurrence from hydrogen, $C_1$-$C_6$ linear or branched alkyl, $C_2$-$C_6$ alkenyl, $C_2$-$C_6$ alkynyl, benzyl, —WR$_5$, halo, thiomethyl, hydroxy, or —O—($C_1$-$C_{10}$ alkyl) or phenyl, and $R_7$ and $R_8$ are independently selected at each occurrence from H or $C_1$-$C_3$ alkyl; and Halo is —F, —Cl, —Br, or —I.

The salts described above are preferably pharmaceutically acceptable salts.

Further provided by this invention is a method for treating inflammation or other disease states mediated by the excessive release of $LTB_4$ agonist, such disease states including, but not necessarily limited to, psoriasis, inflammatory bowel disease, asthma, arthritis, chronic lung diseases, sepsis, septic shock, endotoxic shock, and adult respiratory distress syndrome (ARDS).

In each of these diseases there is some evidence of an excessive release of leukotriene $B_4$. This excessive release refers to an amount of leukotriene $B_4$ sufficient to cause a particular condition associated with such an amount. The amount of $LTB_4$ which is considered to be excessive will depend upon a number of factors including the amount of leukotriene required to cause a particular condition, the species of mammal involved, and the susceptibility of the mammal involved. As will be appreciated by those skilled in the art, the success of treating the mammals suffering from or susceptible to a condition characterized by an excessive release of leukotriene B4 with the compounds of the Formula above will be measured by the regression or prevention of the symptoms of such a condition.

This invention also provides for pharmaceutical formulations which comprise as an active ingredient one or more compounds of this invention, and/or pharmaceutically acceptable salts thereof, associated or admixed with one or more pharmaceutically acceptable fillers, inerts, excipients, solvents, lubricants, or mixtures thereof and carriers therefor.

DETAILED DESCRIPTION AND PREFERRED EMBODIMENT

The present invention preferably is a series of new organic compounds, and their pharmaceutical formulations and use in the treatment of inflammation and in the treatment of disease states caused generally by an excessive release of leukotriene B4 ($LTB_4$). A preferred group of compounds are the compounds having the structural formula:

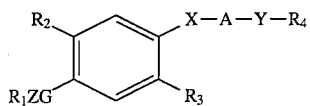

wherein:

X and Y are the same or different and are individually selected at each occurrence from —$CH_2$— or —O—;

A is a linear or branched $C_1$-$C_6$ alkylidene;

G is

or —$CH_2$—; and $R_4$ is selected from:

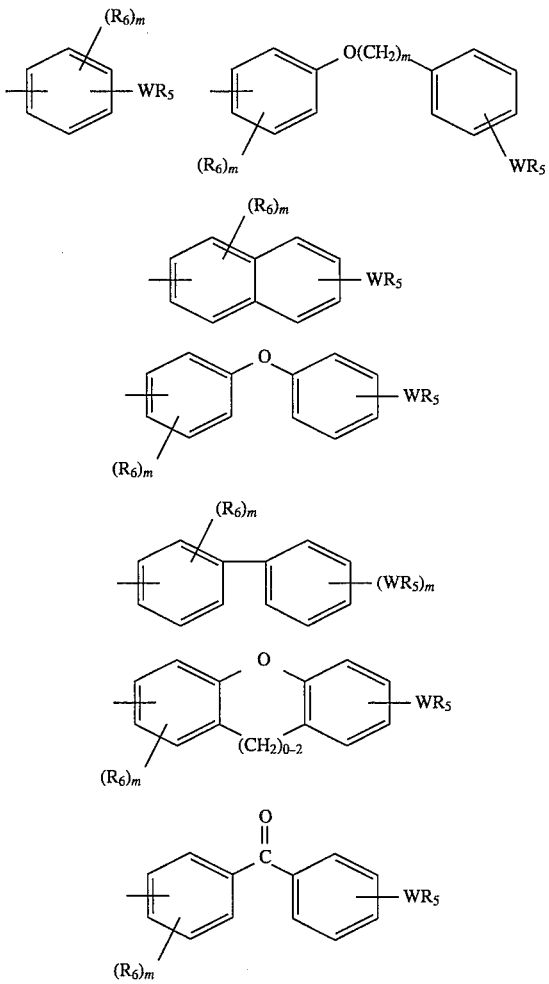

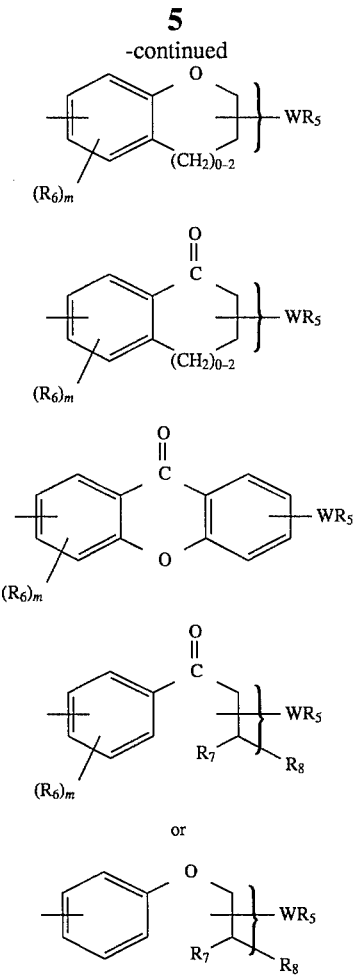

wherein

R₅ is —COOH, and m ranges from 0–2 (unless otherwise indicated) and n ranges from 1–6.

All other meanings of $R_1$, $R_2$, $R_3$, Z, R', R'', R''', $R_5$, and $R_6$ are as described above.

THE MOST PREFERRED COMPOUNDS

The most preferred compounds are those compounds in which —GZR₁ is

$R_2$ is —OH, $R_3$ is —$(CH_2)_{1-2}CH_3$ and XAY— is —O—$(CH_2)_{1-6}$O—; and $R_4$ are those acid moieties found in the Tables below. The compounds which have these structures, or other structures as presented in Tables I and II, and which compounds demonstrate IC₅₀ nanomolar inhibition of [³H]LTB₄ in binding to human PMN's of 200 or below and/or demonstrate a pKi inhibition of [³H]LTB₄ in binding to guinea pig lung membranes of between about 6.0±0.1 and about 9.0±0.1. are particularly preferred.

Those compounds include, but are not limited to, the following compounds:

1. 6-[3-(4-Acetyl-2-ethyl-5-hydroxyphenoxy)propoxy]-9-oxo-9H-xanthene-2-carboxylic acid, or its disodium salt and hydrates.
2. 3-[1-[2-[3-(4-Acetyl-2-ethyl-5-hydroxyphenoxy)propoxy]dibenzofuran]]propanoic acid, or its salts, esters and the like.
3. 4- [3-Propyl-4-[3-(4-acetyl-2-ethyl-5-hydroxyphenoxy)propoxy]phenoxy]benzoic acid or its salts and hydrates.
4. 4-[4-[3-(4-Acetyl-2-ethyl-5-hydroxyphenoxy)propoxy] phenoxy]benzoic acid or its salts or hydrates;
5. 2-[3-[3-(4-Acetyl-2-ethyl-5-hydroxyphenoxy)propoxy]-phenoxy]benzoic acid or its mono- or di-sodium salts and its hydrates.
6. 7-[3-(4-Acetyl-2-ethyl-5-hydroxyphenoxy)propoxy]-3,4-dihydro-8-propyl-2H- 1-benzopyran-2-carboxylic acid or its sodium salts and/or hydrates.

Similar compounds having excellent antagonistic properties against LTB₄ are exemplified below.

The following definitions refer to the various terms used throughout this disclosure.

The term "$C_1$-$C_{10}$ alkyl" refers to the straight and branched aliphatic radicals of 1 to 10 carbon atoms such as methyl, ethyl, propyl, isopropyl, butyl, isobutyl, sec-butyl, tert-butyl, amyl, isoamyl, sec-amyl, sec-isoamyl (1,2-dimethylpropyl), tert-amyl (1,1-dimethylpropyl), hexyl, isohexyl (4-methylpentyl), sec-hexyl (1-methylpentyl), 2-methylpentyl, 3-methylpentyl, 1,1-dimethylbutyl, 2,2-dimethylbutyl, 3,3-dimethylbutyl 1,2-dimethylbutyl, 1,3-dimethylbutyl, 1,2,2-trimethylpropyl, 1,1,2-trimethylpropyl, heptyl, isoheptyl (5-methylhexyl, sec-heptyl(1-methylhexyl), 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, isooctyl (6-methylheptyl), sec-octyl, (1-methylheptyl) , tert-octyl (1,1,3,3-tetramethylbutyl), nonyl, 1-, 2-, 3-, 4-, 5-, 6-, or 7-methyloctyl, 1-, 2-, 3-, 4-, or 5-ethylheptyl, 1-, 2-, or 3-propylhexyl, decyl, 1-, 2-, 3-, 4-, 5-, 6-, 7-, or 8-methylnonyl, 1-, 2-, 3-, 4-, 5-, or 6-ethyloctyl, 1-, 2-, 3-, or 4-propylheptyl, and the like. The term "$C_1$-$C_{10}$ alkyl" includes within its definition the terms "$C_1$-$C_3$ alkyl", "$C_1$-$C_4$ alkyl", and "$C_1$-$C_6$ alkyl".

The term "$C_1$-$C_4$ alkoxy" refers to methoxy, ethoxy, propoxy, isopropoxy, butoxy, sec-butoxy, isobutoxy, and tert-butoxy. The term "$C_1$-$C_4$ alkoxy" includes within its definition the terms "$C_1$-$C_3$ alkoxy" or "$C_1$-$C_2$ alkoxy".

The term "halo" refers to fluoro, chloro, bromo, and iodo.

The term "$C_2$-$C_6$ alkenyl" refers to straight and branched radicals of two to six carbon atoms such as ethenyl, allyl, isopropenyl, butenyl, isobutenyl, 3-methyl-2-butenyl, n-hexenyl, and the like.

The term "$C_2$-$C_6$ alkenyl" refers to straight and branched aliphatic radicals of 2 to 6 carbon atoms containing one double bond, such as —CH=CH₂, —CH₂CH=CH₂, —CH₂CH₂CH=CH₂, —CH₂C(CH₃)=CH₂, —CH₂CH=C(CH₃)₂, and the like.

The term "$C_2$-$C_6$ alkynyl" refers to groups such as acetylenyl, propargyl, butynyl, hexynyl, and the like.

The term "$C_2$-$C_6$ alkynyl" refers to straight and branched aliphatic residues of 2 to 6 carbon-atoms containing one triple bond, such as —C≡CH, —CH₂—C≡CH, —CH₂CH₂C≡CH, —CH₂CH(CH₃)C≡CH, —CH₂C≡CCH₃, —CH₂C—C≡C—CH₂CH₃ and the like.

The term "$C_1$-$C_6$ alkanoyl" refers to the straight and branched aliphatic acyl radicals of 1 to 6 carbon atoms such as formyl, acetyl, propionyl, butyryl, 2-methylpropionyl, pentanoyl, hexanoyl, and the like.

The terms "$C_1$-$C_{10}$ alkylidene" and phenylene are divalent radicals derived from (a) $C_1$-$C_{10}$ alkanes, both linear and branched;
(b) $C_1$-$C_{10}$ alkenes, both linear and branched;
(c) $C_1$-$C_{10}$ alkynes, both linear and branched;
(d) or mixtures thereof, limited to no more than 10 carbon atoms; and (e) benzene, such as 1–4 phenylene, or 1–3 phenylene.

Within the definitions of the term "$C_1$-$C_{10}$ alkylidene" is included a divalent radical derived from any $C_1$-$C_{10}$ alkane such as —$CH_2$—, —$CH(CH_3)$—, —$C(CH_3)_2$—, —$CH(C_2H_5)$—, —$CH_2CH_2$—, —$CH_2CH(CH_3)$—, —$CH(CH_3)CH_2$—, —$CH(CH_3)CH(CH_3)$—, —$CH_2C(CH_3)_2$—, —$CH_2CH(C_2H_5)$—, —$CH_2CH_2CH_2$—, —$CH(CH_3)CH_2CH_2$—, —$CH_2CH(CH_3)CH_2$—, —$CH_2CH(C_2H_5)CH_2$—, —$CH_2CH_2CH(C_2H_5)$—, —$C(CH_3)_2CH_2CH_2$—, —$CH(CH_3)CH_2CH(CH_3)$—, —$CH_2CH_2CH_2CH_2$—, —$CH_2C(CH_3)_2CH_2CH_2$—, —$CH_2C(CH_3)_2CH_2$—, —$CH_2CH_2CH(C_2H_5)CH_2$—, —$CH_2CH_2CH_2CH_2CH_2$—, —$CH(CH_3)CH_2CH_2CH_2CH_2$—, —$CH_2CH_2CH_2CH_2CH_2$—, —$(CH_2)_{10}$—, and the like. Included within this definition are the terms "$C_1$-$C_6$ alkylidene" and "$C_2$-$C_4$ alkylidene". Also included are structures containing one or more carbon-carbon double or triple bonds, or admixtures of double and triple bonds.

The term "hydroxy" is —OH; and the term "hydroxysubstituted alkyl" refers to an alkyl group, described above, substituted with at least one hydroxyl, —OH, group and containing no more than one hydroxyl group per carbon atom in the chosen alkyl group. The preferred hydroxy substituted alkyl groups are:

(a) —$CH_2OH$,
(b) —$CH_2CH_2OH$,
(c) —$CH_2CH_2CH_2OH$, and
(d) —$CH_2$, —CH—OH. $CH_3$

AROMATIC RING SUBSTITUTION

In the above descriptions, several structural depictions are set forth indicating structural group substituion on aromatic or cyclic, either carbocyclic or heterocyclic, rings.

If, in the above structures, a group is bonded into the center of a ring, i.e.,

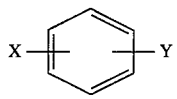

this is to take its normal meaning that, in the example above, X and Y are to be substituted onto a benzene ring in any relationship, i.e., ortho, meta, or para, one to other.

If a structure is shown as:

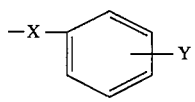

this means, again that Y may be ortho, meta, or para to —X— on the benzene ring.

If

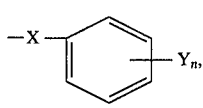

where n=1–5 this is to mean that Y is substituted from 1 to 5 times on the benzene ring, as permitted by normal chemical bonding rules.

In a more particular example, if the structure

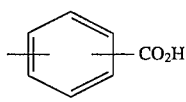

is set forth, this structure is to mean any or all of the following structures:

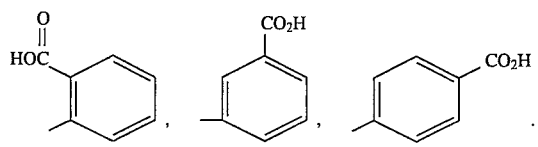

If the structure

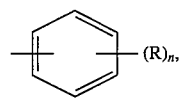

where n=0–4 is set forth, this includes any and all of the structures:

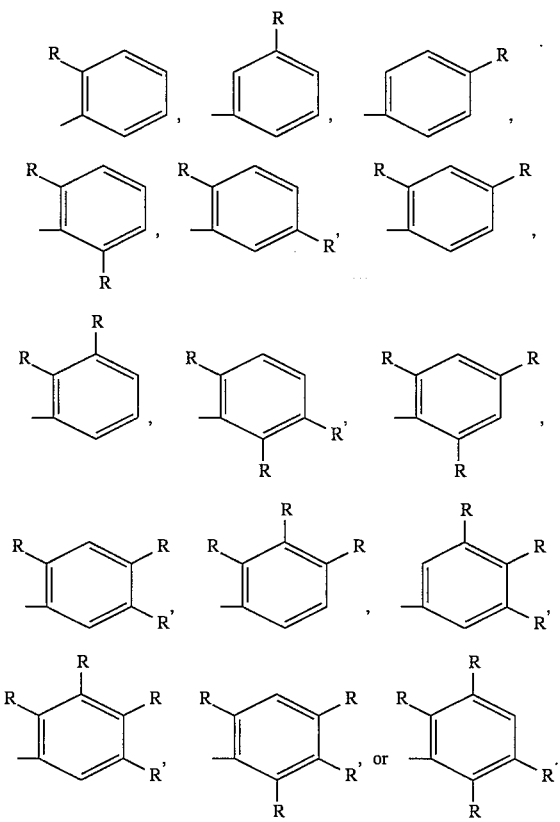

If a structure is set forth as

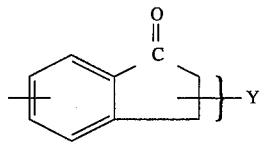

this means that the Y substituent may attach at either of the two ring positions adjacent the brace symbol, "}", and includes, for example, any and all structures in the group:

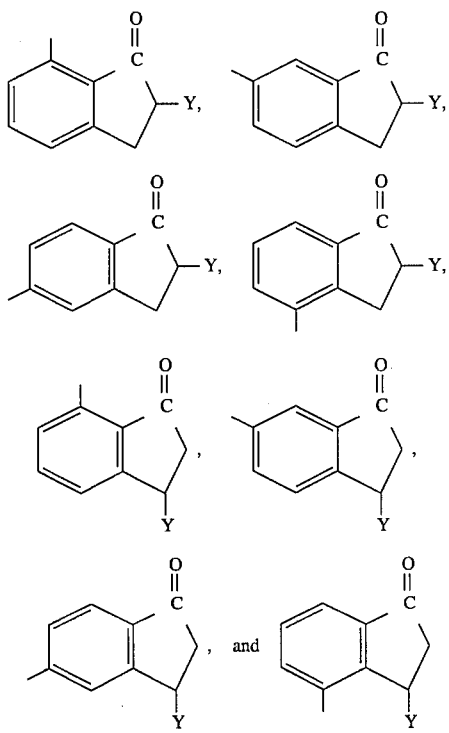

In all such "stick" structures, where lines intersect with no atom shown, carbon is intended at the intersection and hydrogen, normally shown to complete carbons quadravalency, is not shown above, but is presumed to be present to complete this quadravalency for carbon.

When structures are shown

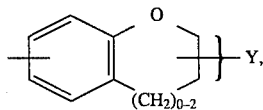

this is to include any and all of the structures:

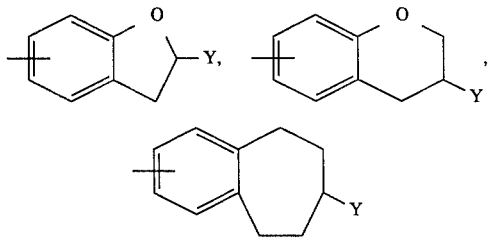

with all options for aromatic ring and Y bonding included, as taught above.

It is believed that all structures shown herein may be properly interpreted using the above guidelines. It is also believed that these so-called "stick structures" are used commonly in the art and all structures herein described are easily interpreted within the scope of knowledge of the artisan.

This invention includes the pharmaceutically acceptable base addition salts of the compounds of each formulae presented above. Such salts include those derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred. This invention includes both monosalt forms, i.e., a 1:1 Molar ratio of each compound of the Formulas above with a base as previously described, as well as di-salt forms in those instances where the representative compounds has two acidic groups. In addition, this invention includes any solvate forms of the compounds represented above or salts thereof, such as ethanol solvates, hydrates, and the like.

It is recognized that in compounds having branched alkyl, alkylidenyl, or other branched hydrocarbyl functionality, and in those compounds bearing double or triple bonds, various stereoisomeric products may exist. This invention is not limited to any particular stereoisomer but includes all possible individual isomers and mixtures thereof. Likewise, in structures containing carbon-carbon double bonds, both cis and trans isomers, and mixtures thereof, are also included in this invention. The term "5-tetrazolyl" refers to both tautomers, i.e., (1H)-5-tetrazolyl and (2H)-5-tetrazolyl.

COMPOUND SYNTTHESIS

The compounds of this invention may be prepared according to standard methods known in the art. For example, the tetrazole compounds of our Formulas (wherein at least one $R_5$ is 5-tetrazolyl) may be prepared from the corresponding intermediate, wherein the corresponding $R_5$ group contains a nitrile group by any of a variety of standard methods. Generally, the nitrile is reacted with an azide reagent in a non-reactive solvent. Preferred conditions include the use of lithium or ammonium azide in dimethylformamide, sodium azide in diglyme and N,N-dimethylethanolamine hydrochloride, or tri-n-butyltin azide in a non-reactive solvent such as dimethoxyethane or tetrahydrofuran. Under the latter conditions, the reaction is generally heated at or near the reflux temperature of the reaction mixture. The transformation is generally complete under these conditions in 2–3 days. Other operable reaction conditions include the reaction of the appropriate nitrile with an alkali metal azide such as sodium azide, ammonium chloride, and (optionally) lithium chloride in a non-reactive high-boiling solvent such as N,N-dimethylformamide (DMF), preferably at temperatures from about 60° C. to about 125° C. Alternatively, tri-n-butyltin azide or tetramethylguanidinium azide, in a solvent such as tetrahydrofuran, dimethoxyethane, diethoxyethane, or the like, may be used in place of the alkali metal azide, ammonium chloride, lithium chloride and DMF.

Similarly, the acids of this invention, (wherein at least one $R_5$ is —COOH) are prepared from the corresponding intermediates wherein the corresponding $R_5$ group is —COOR or —CN. Hydrolysis of such esters or nitriles may be accomplished by any of a variety of acidic or basic conditions, preferably under aqueous conditions. Preferred methods involve the use of lithium hydroxide in a solvent mixture of acetone/water, sodium hydroxide in dioxane, or potassium hydroxide or potassium carbonate in a mixture of methanol/water. Under the former conditions, hydrolysis is generally complete in about 12–18 hours at temperatures from about 20°–30° C. whereas the latter reaction is usually complete in one hour at 20°–30° C.

It is generally preferred, in compounds containing both a nitrile and an ester functionality, that the nitrile group be transformed into a tetrazole before hydrolysis of the ester. To further exemplify the synthetic routes and the reactions used to obtain compounds later tested, the following synthetic routes and examples are presented:
Scheme 1
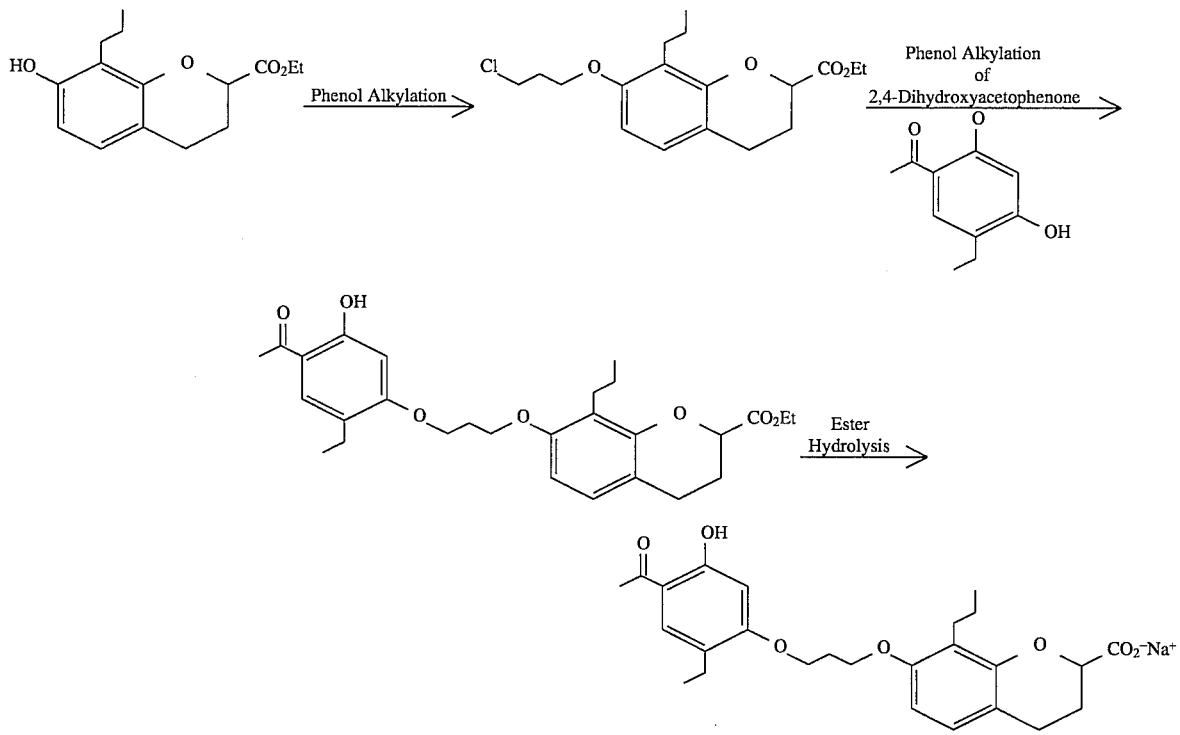
Scheme 2
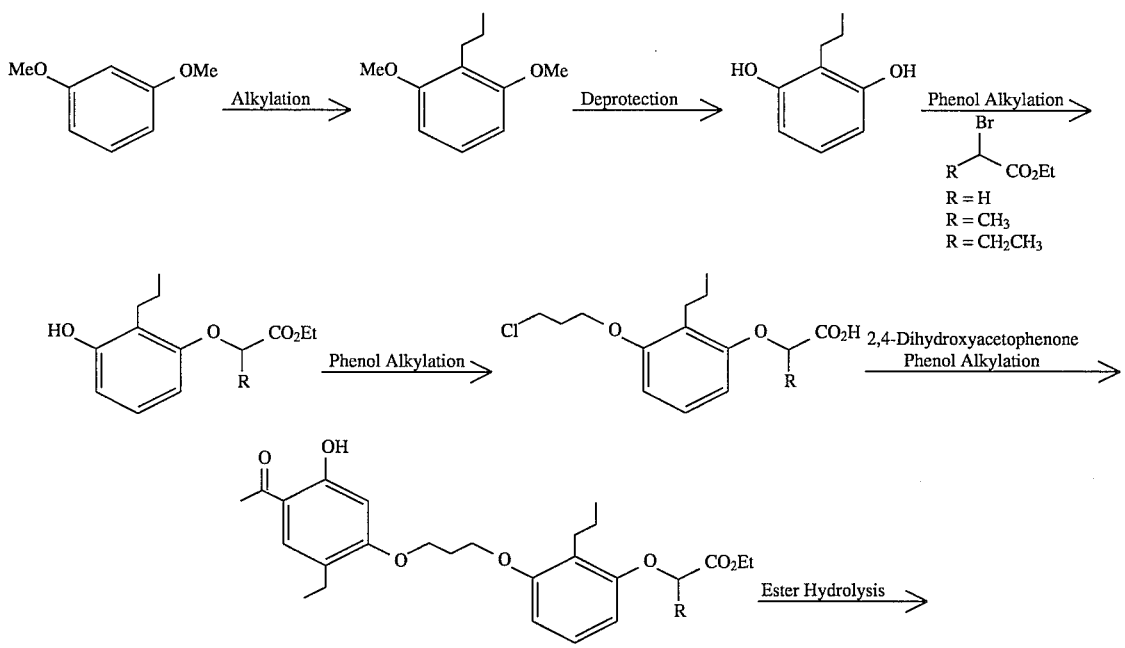

-continued
Scheme 2

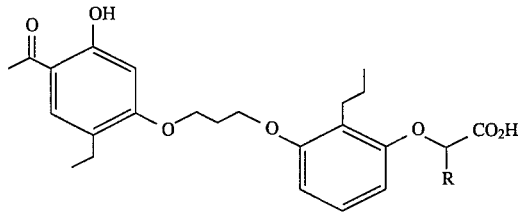

Synthesis Summary

To exemplify these general steps, a general procedure outlined above attaches the acid containing unit $R_4$ to a hydroxy acetophenone unit (Synthetic Schemes 1 and 2 above). A hydroxy acetophenone unit is preferably attached as in Scheme 1 and 2 above in a so-called phenol alkylation of 2,4-dihydroxyacetophenone reaction. These structures are exemplary of the compounds of our invention, but do not limit the invention. Other exemplary synthetic processes and procedures follow.

In addition, various compounds of our Formulas can be prepared from other compounds, precursors, or intermediates of our Formulas by standard methods such as hydrolysis, esterification, alkylation, oxidation, reduction, and the like, as are well known to those skilled in the art. The Schemes noted above are illustrative of the more conventional methods for preparing the compounds of this invention. However, different combinations of these chemical steps and others generally known in the organic chemistry art can effectively be employed; the particular sequence of any such transformations and interconversions will be appreciated by experienced organic chemists in view of the various functional groups to be present in the compound of choice. For example, a tetrazole group can be protected with a group such as trityl; other chemistry can be performed on the remaining portion of the molecule, and the trityl group removed upon treatment with dilute acid to give the unprotected tetrazole. Other variations of this and related transformations will be apparent to skilled artisans in this field.

The following preparations and examples further illustrate the preparation of the intermediates and compounds of this invention. The examples are illustrative only and are not intended to limit the scope of the invention. Melting points were determined on a Thomas-Hoover apparatus and are uncorrected. NMR spectra, both above and hereinafter, were determined on a GE QE-300 spectrometer. All chemical shifts are reported in parts per million ($\partial$) relative to tetramethylsilane. The following abbreviations are used to denote signal patterns: s=singlet, d=doublet, t=triplet, q=quartet, b=broad, m=multipier. Infrared spectra were determined on a Nicolet DX10 FT-IR spectrometer. Mass spectral data were determined on a CEC-21-110 spectrometer using electron impact (EI) conditions, a MAT-731 spectrometer using free desorption (FD) conditions, or a VG ZAB-3F spectrometer using fast atom bombardment (FAB) conditions. Silica gel chromatography was performed using ethyl acetate/hexane gradients unless otherwise indicated. Reverse-phase chromatography was performed on MCI CHP20P gel using an acetonitrile/water or methanol/water gradient unless otherwise indicated. Tetrahydrofuran (THF) was distilled from sodium/benzophenone ketyl immediately prior to use. All reactions were conducted under argon atmosphere with stirring unless otherwise noted. Where structures were confirmed by infra-red, proton nuclear magnetic resonance, or mass spectral analysis, the compound is so designated by "IR", "NMR", or "MS", respectively.

EXAMPLE 1

Preparation of
7-[3-(4-acetyl-2-ethyl-5-hydroxyphenoxy)propoxy]-
3,4-dihydro-
8-propyl-2H-1-benzopyran-2-carboxylic acid.

A. Preparation of Chromone.

To a solution of 225 mL of EtOH(Anhydrous) under argon atmosphere and at room temperature added 16.56 g of Na metal over a 1 hour. period. After all of the Na was added the reaction mixture was refluxed for 1 hour. then cooled to room temperture. A mixture of 2,4-dihydroxyacetophenone (34.82g, 0.180 mol), diethyloxylate (54.57 mL, 0.41 mol), absolute EtOH (45 mL), and diethylether (45 mL) was added to the sodium ethoxide solution over 25 min. The resulting deep maroon reaction mixture was then refluxed for 2.5 h and then cooled to room temp. The reaction mixture was poured into approx. 600 mL of 1N HCl and then extracted several times with $Et_2O$. The ether was removed form the extract and the resulting gum was dissolved in 135 mL of EtOH. To this solution was then added 2.25 mL of conc. HCl and subsequently refluxed for 45 min.. The reaction was cooled to room temp and EtOH was removed under reduced pressure leaving a brown solid. This solid was dissolved in EtOAc and washed one time with $H_2O$, two times with sat'd $NaHCO_3$, one time with $H_2O$ and then dried over $MgSO_4$. Filtration and solvent removal gave 87 g of a brown solid which was recrystallized from EtOAc/petroleum ether. Recrystallization provided 24.07 g (48%) of a tan solid chromone.

TLC: Rf=0.27 (40% EtOAc/Hexane). $^1$H NMR ($CDCl_3$) $\delta$8.80 (s(br), 1), 7.98 (d, 1, J=8.78 Hz), 7.13 (d, 1, J=8.78 Hz), 7.13 (s, 1), 4.47 (q, 2, J=7.11 Hz), 2.96 (t, 2, J=7.25 Hz), 1.73 (m, 2), 1.46 (t, 3, J=7.16 Hz), 1.02 (t, 3, J=7.11 Hz).

B. Preparation of Ethyl 3,4-dihydro-8-propyl-2H-1-benzopyran-2-carboxylate.

In a pressure bottle, the chromone (12.07 g, 0.044 mol) was dissolved in 210 mL of acetic acid. 10% Pd/C (7.2 g) catalyst was added to this solution and the bottle was pressurized with 52 psi of $H_2$ gas. The reaction was agitated for 23 hours. The catalyst was removed by filtration through a celite pad in a sintered glass funnel. The catalyst was washed with EtOAc. The solvent was removed from the filtrate and the resulting oil was azeotroped with toluene providing 12 g of brown oil. The material was purified on a Waters Prep 500 HPLC, equiped with silica gel cartridges, running a 5% to 40% EtOAc/Hexane gradient over 50 min at a flow rate of 250 mL/min and collecting 500 mL fractions. The purified chroman was obtained as a pink oil (10 g, 86%).

TLC: Rf=0.50 (40% EtOAc/Hexane). 1H NMR (CDCl3) δ6.73 (d, 1, J=8.20 Hz), 6.37 (d, 1, J=8.20 Hz), 4.78 (s(br), 1), 4.75 (m, 1), 4.25 (m, 2), 2.68 (m, 4 ), 2.16 (m, 2), 1.60 (m, 2 ), 1.29 ( t, 3, J=7.07 Hz), 0.99 (t, 3, J=7.34 Hz).

C. Ethyl 7-(3-chloropropoxy)-3,4-dihydro-8-propyl-2H-1-benzopyran-2-carboxylate.

A solution (0.3M) of ethyl 3,4-dihydro-8-propyl-2H-1-benzopyran-2-carboxylate in dry DMF was stirred under argon atmosphere and at room temperature with solid $K_2CO_3$ (1.75 eqv). To this suspension added 1-bromo-2-chloropropane (2.5 eqv.). The reaction was stirred at room temperature fro 20 h and then quenched with water. The reaction mixture was extracted with EtOAc (three times), and the ethyl acetate extract was washed with water and then dried over $MgSO_4$. Filtration and solvent removal gave the crude product as an oil which was purified by flash chromatography on silica gel eluting with 15% EtOAc/Hexane. Ethyl 7-(3-chloropropoxy)-3,4-dihydro-8-propyl-2H-1-benzopyran-2-carboxylate was prepared in 72% yield.

$^1$H NMR (CDCl$_3$) δ 6.83 (d,1,J=8.96 Hz), 6.48 (d,1,J= 8.96 Hz), 4.77 (t, 1, J=5.52 Hz), 4.67 (m,2), 4.10 (t, 2, J=5.52 Hz), 3.80 (t, 2, J=5.50 Hz) 2.70 (m, 4), 2.26 (m, 4), 1.6 (m, 2) ,1.28 (t, 3, J=7.36 Hz), 0.98 (t, 3, J=6.44 Hz) IR (CHCl$_3$) 2963, 2933, 1749, 1728, 1612 cm$^{-1}$ Mass Spec (FAB) (m/z) 341 (M$^+$+H), 340(M+)

D. Ethyl 7-[3-(4-acetyl-2-ethyl-5-hydroxyphenoxy)propoxy]-3,4-dihydro-8-propyl- 2H-1-benzopyran-2-carboxylate.

To a solution of 2,4-dihydroxy-4-ethyl acetophenone in 5:1 methylethylketone and DMSO (0.45M soln) at room temp added the chloropropyl ether (1.0 eqv), $K_2CO_3$ (1.75 eqv) and KI (0.20 eqv). The reaction was then refluxed for 20 hours. The reaction was then cooled to room temperature and quenched with water. The reaction mixture was extracted with EtOAc (three times) and this extract was washed with water and then dried over MgSO4. Filtration and solvent removal gave a crude product which was purified by flash chromatography on silica gel-eluting with 20% EtOAc/Hexane. Ethyl 7-[3-(4-acetyl-2-ethyl-5-hydroxyphenoxy)propoxy]-3,4-dihydro-8-propyl- 2H-1-benzopyran-2-carboxylate was prepared in 73% yield.

$^1$H NMR (CDCl$_3$) δ7.43 (S,1), 6.81 (d,1,J=8.39 Hz), 6.47 (d, 1, J=8.39 Hz), 6.42 (s, 1), 4.75 (m, 1), 4.24 (m, 4), 4.14 (t, 2, J=5.98 Hz), 2.64 (m, 6), 2.58 (s, 3), 2.35 (m, 2), 2.20 (m, 2), 1.55 (m, 2), 1.29 (t, 3, J=7.14 Hz), 1.18 (t, 3, J=7.47 Hz), 0.93 (t, 3, J=7.34 Hz). IR (CHCl$_3$) 2961, 2931, 2862, 1746, 1715, 1631, 1569 cm$^{-1}$ Mass Spec (FAB) (m/z) 485 (M$^+$+H), 484 (M$^+$) Elem Anal Calc'd for $C_{28}H_{36}O_7$: C, 69.40; H, 7.49 Found: C, 70.23, H, 8.08

E. 7-[3-(4-acetyl-2-ethyl-5-hydroxyphenoxy)propoxy]-3,4-dihydro-8-propyl- 2H-1-benzopyran-2-carboxylic acid.

A solution of ethyl 7-[3-(4-acetyl-2-ethyl-5-hydroxyphenoxy)propoxy]-3,4-dihydro-8-propyl- 2H-1-benzopyran-2-carboxylic in dioxane (3.5M solution) was treated with 2N NaOH (3.0 eqv) and stirred at room temperature. After stirring for 4 hours, the dioxane was removed from the reaction, and the remaining solution was diluted with water and acidified with 5N HCl. The resulting milky solution was extracted with EtOAc. The ethyl acetate extract was dried over $MgSO_4$ and filtered. Solvent removal gave a white solid. The solid was purified by flash chromatography on silica gel eluting with 50% EtOAc/Hexane, and the resulting solid was crystalized from EtOAc and hexane. The desired acid was obtained in 47% yield.

$^1$H NMR (CDCl$_3$) δ12.72 (s, 1), 7.44 (s,1), 6.86 (d, 1, J=8.30 Hz), 6.51 (d, 1, J=8.30 Hz), 6.40 (s, 1), 4.75 (dd, 1, J=9.18 Hz, 4.59 Hz), 4.23 (t, 2, J=5.74 Hz), 4.15 (t, 2, J=5.74 Hz), 2.80 (m, 1), 2.62 (m, 2), 2.60 (s, 3), 2.58 (m, 2), 2.35 (m, 2), 2.13 (m, 1), 1.55 (m, 2), 1.31 (t, 3, J=6.90 Hz), 1.20 (t, 3 , J=8.04 Hz), 0.95 (t, 3, J=8.04 Hz) IR (CCl$_4$) 3020, 3000, 2945, 3000, 1775, 1725, 1633, 1615 cm$^{-1}$ Mass Spec (FD) (m/z) 456 (M$^+$) Elem Anal Calc'd for $C_{26}H_{32}NO_7$: C, 68.40; H, 7.06 Found: C, 68.61; H, 7.22

EXAMPLE 2

Preparation of
7-[3-(4-acetyl-2-ethyl-5-hydroxyphenoxy)propoxy]-
3,4-dihydro-
8-propyl-2H-1-benzopyran-2-carboxylic acid
sodium salt.

A. 7-[3-(4-acetyl-2-ethyl-5-hydroxyphenoxy)propoxy]-3,4-dihydro-8-propyl-2H- 1-benzopyran-2-carboxylic acid sodium salt.

A solution of ethyl 7-[3-(4-acetyl-2-ethyl-5-hydroxyphenoxy)propoxy]-3,4-dihydro-8-propyl- 2H-1-benzopyran-2-carboxylate in dioxane (3.5M solution) was treated with 2N NaOH (3.0 eqv) and stirred at room temperature. After stirring for 4 hours, the dioxane was removed from the reaction, and the remaining solution was diluted with water and acidified with 5N HCl. The resulting milky solution was extracted with EtOAc. The ethyl acetate extract was dried over $MgSO_4$ and filtered. Solvent removal gave a white solid. The free acid was stirred in methanol and treated with 3 eqv. of NaOH(aq). The solvent was removed from the reaction and the product was purified by CHP-20 reverse phase chromatography eluting with a water/methanol gradient. The pure product was obtained in 68% yield by lyophilization of the product containing fractions.

$^1$H NMR (d$^6$-DMSO) δ7.58(s, 1), 6.67 (d, 1, J=8.36 Hz), 6.49 (s, 1), 6.35 (d, 1, J=8.36 Hz), 4.23 (m, 1), 4.17 (t, 2, J=5.94 Hz) 4.03 (t, 2, J=6.91 Hz), 2.52 (s, 3), 2.48 (m, 6), 2.15 (m, 2), 2.00 (m, 1), 1.95 (m, 1), 1.40 (m, 2), 1.07 (t, 3, J=7.40 Hz), 0.78 (t, 3, J=7.28 Hz) Elem Anal Calc'd for $C_{26}H_{31}O_7Na$: C, 65.26; H, 6.53 Found: C, 65.55; H, 6.58

Preparation of 2-Propyl-1,3-dimethoxybenzene.

1,3-Dimethoxybenzene (20 g, 145 mmol) in 200 mL of dry tetrahydrofuran was cooled to −10° C. To this solution at −10° C. added nBuLi (100 mL of a 1.6M solution in Hexane, 160 mmol ) over 20 min. The reaction was then stirred for 2.5 hours at 0° C. At 0° C., propyliodide (24.65 g, 145 mmol ) was added slowly over 15 min. When the addition was complete, the reaction was allowed to warm to room temperature and stirred overnight. After stirring overnight, the reaction was refluxed for 1.5 hour then cooled to room temperature and quenched with ice. The THF was remove under vacuum, and the resulting aqueous layer was extracted several times with Et$_2$O. The organic extract was dried over $MgSO_4$ and filtered to give a clear oil after solvent removal (26.11 g). The oil was purified by vacuum distillation (24.0 g, 92%).

Bpt. 80°–82° C. at 10 mmHg. $^1$H NMR (CDCl$_3$) δ7.16 (t, 1, J=8.30 Hz), 6.58 (d, 2, J=8.30 Hz), 3.85 (s, 6), 2.67 (t, 2, J=7.57 Hz), 1.56 (m, 2 ), 0.99 (t, 3, J=7.35 Hz ).

Preparation of 2-Propyl-1,3-Dihydroxybenzene.

A mixture of solid 1,3-dimethoxy-2-propylbenzene (33.70 g, 190 mmol) and solid pyridine hyrochloride (150 g, 1.30 mol) were warmed to 180° C. After 7.5 hours, the reaction was cooled to 110° C. and 50 mL of H$_2$O was added slowly. After the reaction cooled to room temperature, it was diluted with 100 mL of water and extracted several times with EtOAc. The EtOAc extract was washed once with 2N HCl and then dried over $MgSO_4$. Filtration and solvent removal gave 38.5 g of an orange solid. The product was purified by recrystallization from dichloromethane providing 11.86 g (41%) of yellow crystals.

$^1$H NMR (CDCl$_3$) δ6.94 (t, 1, J=8.10 Hz), 6.40 (d, 2, J=8.10 Hz), 4.84 (s, 2), 2.63 (t, 2, J=7.57 Hz), 1.62 (m, 2), 1.01 (t, 3, J=7.33 Hz).

EXAMPLE 3

Preparation of 2-[2-propyl-3-[[3-(4-acetyl-2-ethyl-5-hydroxyphenoxy)proyl]oxy]phenoxy]acetic acid.

A. Ethyl 2[2-propyl-3-hydroxyphenoxy]acetate.

Sodium hydride (0.402 g of a 60% oil dispersion, 10 mmol) under argon arm was washed with 15 mL of dry hexane. The hexane supernatant was removed via syringe. Dry THF (40 mL) was added to the Nail and with stirring at room temperature, the dihydroxypropylbenzene (1.527 g, 10 mmol) was added as a 20 mL THF solution. After stirring at room temp for 25 minutes, the ethyl 2-bromo-acetate (1.59 g, 9.5 mmol) was added rapidly. After stirring at room temperature for 17 hours, the reaction was quenched with saturated aqueous NH$_4$Cl solution, and the THF was removed under vacuum. The resulting aqueous mixture was extracted several times with EtOAc. The organic extract was dried over MgSO$_4$. Filtration and solvent removal gave an orange oil. This oil was purified by flash chromatography on Merck silica gel eluting with 25% EtOAc/Hexane. The desired was obtained as a clear oil (1.260 g g, 53%).

TLC: Rf=0.53 (30% EtOAc/Hexane, Silica gel) $^1$H NMR (CDCl$_3$) δ7.00 (t, 1, J=9.3 Hz), 6.52 (d, 1, J=9.30 Hz), 6.36 (d,1,J=9.30Hz), 5.79 (s,1), 4.69 (s,2), 4.32 (q, 2, J=7.40 Hz), 2.70 (m, 2), 1.63 (m, 2), 1.32 (t, 3, J=7.40 Hz), 1.00 (t, 3, J=7.40 Hz)

B. Ethyl 2-[2-propyl-3-(3-chloropropyloxy)phenoxy]acetate.

A solution (0.3M) of ethyl 2[2-propyl-3-hydroxyphenoxy]acetate in dry DMF was stirred under argon atmosphere and at room temperature with solid K$_2$CO$_3$ (1.75 eqv). To this suspension added 1-bromo-3-chloropropane (2.5 eqv.). The reaction was stirred at room temperature fro 20 hours and then quenched with water. The reaction mixture was extracted with EtOAc (three times), and the ethyl acetate extract was washed with water and then dried over MgSO$_4$. Filtration and solvent removal gave the crude product as an oil which was purified by flash chromatography on silica gel eluting with 15% EtOAc/Hexane. The desired product was prepared in 33% yield.

$^1$H NMR (CDCl$_3$) δ7.10 (t, 1, J=8.31 Hz), 6.59 (d, 1, J=8.30 Hz), 6.43 (d, 1, J=8.30 Hz), 4.65 (s, 2), 4.27 (q, 2, J=7.12 Hz), 4.11 (t, 2, J=5.70 Hz), 3.79 (t, 2, J=6.40 Hz), 2.76 (t, 2, J=7.36 Hz), 2.26 (m, 2), 1.62 (m, 2), 1.36 (t, 3, J=7.14 Hz), 1.01 (t, 3, J=7.35 Hz), IR (CHCl$_3$) 3019, 2966, 2934, 2872, 1757, 1733, 1594 cm$^{-1}$ Mass Spec (FAB)(m/z) 315 (M$^+$+H), 314 (M$^+$), Elem Anal Calc'd for C$_{16}$H$_{23}$O$_4$C$_1$: C, 61.05; H, 7.36; Cl, 11.26; Found: C, 61.04; H, 7.31; Cl, 11.40

C. Ethyl 2-[2-propyl-3-[[3-(4-acetyl-2-ethyl- 5-hydroxyphenoxy)propyl]oxy]phenoxy]acetate.

To a solution of 2,4-dihydroxy-4-ethyl acetophenone in 5:1 methylethylketone and DMSO (0.45M solution) at room temp added ethyl 2-[2-propyl-3-(3-chloropropyloxy)phenoxy]acetate (1.0eqv), K$_2$CO$_3$ (1.75 eqv) and KI (0.20 eqv). The reaction was then refluxed for 20 hours. The reaction was then cooled to room temperature and quenched with water. The reaction mixture was extracted with EtOAc and this extract was washed with water and then dried over MgSO$_4$. Filtration and solvent removal gave a crude product which was purified by flash chromatography on silica gel eluting with 20% EtOAc/Hexane. Ethyl 2-[2-propyl-3-[[3-(4-acetyl-2-ethyl- 5-hydroxy-phenoxy)propyl]oxy]phenoxy]acetate was prepared in 62% yield.

$^1$H NMR (CDCl$_3$) δ12.74 (s, 1), 7.43 (s, 1), 7.08 (t, 1, J=8.33 Hz), 6.58 (d, 1, J=8.10 Hz), 6.42 (s, 1), 6.41 (d, 1, J=8.10 Hz, 4.63 (s, 2), 4.25 (m, 4), 4.17 (t, 2, J=5.98 Hz), 2.72 (t, 2, J=7.36 Hz), 2.58 (m, 2), 2.56 (s, 3), 2.33 (m, 2), 1.56 (m, 2), 1.29 (t, 3, J=7.08 Hz), 1.18 (t, 3, J=7.50 Hz), 0.95 (t, 3, J=7.33 Hz) IR (KBr) 3400, 2963, 2868, 1741, 1637, 1597 cm$^{-1}$ Mass Spec (FAB) (m/z) 459 (M$^+$+H)

D. 2-[2-Propyl-3-[[3-(4-acetyl-2-ethyl-5-hydroxyphenoxy)proyl]oxy]phenoxy]acetic acid.

A solution of ethyl 2-[2-propyl-3-[[3-(4-acetyl-2-ethyl-5-hydroxy-phenoxy)propyl]oxy]phenoxy]acetaete in dioxane (3.5M solution) was treated with 2N NaOH (3.0 eqv) and stirred at room temperature. After stirring for 4 hours the dioxane was removed from the reaction, and the remaining solution was diluted with water and acidified with 5N HCl. The resulting milky solution was extracted with EtOAc. The ethyl acetate extract was dried over MgSO4 and filtered. Solvent removal gave a white solid. The solid was purified the by crystalization from EtOAc and hexane. The desired acid was obtained in 78% yield.

$^1$H NMR (CDCl$_3$) δ12.51 (s, 1), 7.25 (s, 1), 6.87 (t, 1, J=8.33 Hz), 6.37 (d, 1, J=8.29 Hz), 6.23 (d, 1, J=8.30 Hz), 6.20 (s, 1), 4.39 (s, 2), 4.03 (t, 2, J=6.02 Hz), 3.97 (t, 2, J=6.00 Hz), 2.47 (m, 2), 2.37 (s, 3), 2.36 (m, 2), 2.12 (m, 2), 1.30 (m, 2), 0.97 (t, 3, J=7.47 Hz), 0.72 (t, 3, J=7.32 Hz) IR (KBr) 3415, 2964, 2930, 2870, 1738, 1715, 1637 cm$^{-1}$ Mass Spec (FAB) (m/z) 431 (M$^+$+H)

Elem Anal Calc'd for C$_{24}$H$_{30}$O$_7$: C, 66.96; H, 7.02 Found: C, 67.22; H, 7.22

EXAMPLE 4

Preparation of 2-[3-[3-(4-acetyl-2-ethyl-5-hydroxyphenoxy)propoxy)-2-propylphenoxy]propanoic acid.

A. Ethyl 2[2-propyl-3-hydroxyphenoxy]propionoate.

Sodium hydride (1.08 g of a 60% oil dispersion, 27 mmol) under argon atmosphere was washed with 15 mL of dry hexane. The hexane supernatant was removed via syringe. Dry THF (60 mL) was added to the NaH and with stirring at room temperature, the dihydroxypropylbenzene (4.08 g, 27 mmol) was added as a 40 mL THF solution. After stirring at room temperature for 25 minutes, the ethyl 2-bromoproprionate (4.64 g, 26 mmol) was added rapidly. After stirring at room temperature for 17 hours, the reaction was quenched with saturated aqueous NH$_4$Cl solution, and the THF was removed under vacuum. The resulting aqueous mixture was extracted several times with EtOAc. The organic extract was dried over MgSO$_4$. Filtration and solvent removal gave an orange oil. This oil was purified by flash chromatography on Merck silica gel eluting with 20% EtOAc/Hexane. The desired product was obtained as a white solid (2.43 g, 36%).

TLC: Rf=0.47 (30% EtOAc/Hexane) $^1$H NMR (CDCl$_3$) δ6.93 (dd, 1, J=8.00 Hz), 6.45 (d, 1, J=8.00 Hz), 6.30 (d, 1, J=8.00 Hz), 5.77 (s, 1), 4.76 (q, 1, J=6.76 Hz), 4.23 (q, 2, J=7.02 Hz), 2.69 (m, 2), 1.63 (d, 3, J=6.70 Hz), 1.60 (m, 2), 1.28 (t, 3, J=7.50 Hz , 0.99 (t, 3, J=7.50 Hz); IR (KBr) 3435, 2955, 2872, 1733, 1600, 1500, 1465 cm$^{-1}$; Mass Spec. (FD) (m/z) 253 (M$^+$+1);

Elem Anal. Calc'd for C$_{14}$H$_{20}$O$_4$: C, 66.65; H, 7.99. Found: C, 66.41; H, 8.04.

B. Ethyl 2-[2-propyl-3-(3-chloropropyloxy)phenoxy]proprionate.

A solution (0.3M) of 1,3-dihydroxy-2-propyl benzene in dry DMF was stirred under argon atmosphere and at room temperature with solid $K_2CO_3$ (1.75 eqv). To this suspension added 1-bromo-2-chloropropane (2.5 eqv.). The reaction was stirred at room temperature for 20 hours and then quenched with water. The reaction mixture was extracted with EtOAc (three times), and the ethyl acetate extract was washed with water and then dried over $MgSO_4$. Filtration and solvent removal gave the crude product as an oil which was purified by flash chromatography on silica gel eluting with 15% EtOAc/Hexane. The chloropropylether was prepared in 74% yield.

$^1$H NMR(CDCl$_3$) δ7.05 (t, 1, J=8.26 Hz), 6.55 (d, 1, J=8.26 Hz), 6.37 (d, 1, J=8.26 Hz), 4.74 (q, 1, J=6.81 Hz), 4.21 (q, 2, J=7.08 Hz), 4.11 (t, 2, J=5.71 Hz), 3.78 (t, 2, J=6.40 Hz), 2.69 (m, 2), 2.26 (m, 2), 1.63 (d, 3, J=6.80 Hz), 1.56 (m, 2), 1.26 (t, 3, J=7.21 Hz), 0.96 (t, 3, J=7.35 Hz) IR (CHCl$_3$) 3021, 2965, 1748, 1594 cm$^{-1}$ Mass Spec (FD) (m/z) 328 (M$^+$)

Elem Anal Calc'd for $C_{17}H_{25}O_4Cl$: C, 62.09; H, 7.66, Cl, 10.78 Found: C, 62.06; H, 7.77; Cl, 10.66

C. Ethyl 2-[3-[3-(4-acetyl-2-ethyl-5-hydroxyphenoxy)propoxy)-2-propylphenoxy]propionate.

To a solution of 2,4-dihydroxy-4-ethyl acetophenone in 5:1 methylethylketone and DMSO (0.45M solution) at room temperature added ethyl 2-[2-propyl-3-(3-chloropropyloxy)phenoxy]proprionate (1.0 eqv), $K_2CO_3$ (1.75 eqv) and KI (0.20 eqv). The reaction was then refluxed for 20 hours. The reaction was then cooled to room temperature and quenched with water. The reaction mixture was extracted with EtOAc (three times) and this extract was washed with water and then dried over $MgSO_4$. Filtration and solvent removal gave a crude product which was purified by flash chromatography on silica gel eluting with 20% EtOAc/Hexane. The acetophenone was prepared in 68% yield.

$^1$H NMR (CDCl$_3$) δ12.75 (s, 1), 7.43 (s, 1), 7.05 (t, 1, J=8.26 Hz), 6.56 (d, 1, J=8.27 Hz), 6.42 (s, 1), 6.39 (d, 1, J=8.26 Hz), 4.74 (q, 1, J=6.77 Hz), 4.19 (m, 6), 2.73 (m, 2), 2.58 (m, 2), 2.55 (s, 3), 2.32 (m, 2), 1.63 (d, 3, J=6.75 Hz), 1.60 (m, 2), 1.25 (t, 3, J=7.25 Hz), 1.19 (t, 3, J=7.38 Hz), 0.96 (t, 3, J=7.33 Hz). IR (CHCl$_3$) 2966, 1748, 1633 cm$^{-1}$ Mass Spec (FD) (m/z) 472 (M$^+$)

Elem Anal Calc'd For $C_{27}H_{36}O_7$: C, 68.62; H, 7.68 Found: C, 68.46; H, 7.53

D. 2-[3-[3-(4-Acetyl-2-ethyl-5-hydroxyphenoxy)propoxy)-2-propylphenoxy]propanoic acid.

A solution of ethyl 2-[2-propyl-3-[[3-(4-acetyl-2-ethyl-5-hydroxy-phenoxy)propyl]oxy]phenoxy]propanoate in dioxane (3.5M solution) was treated with 2N NaOH (3.0 eqv) and stirred at room temperature. After stirring for 4 hours the dioxane was removed from the reaction, and the remaining solution was diluted with water and acidified with 5N HCl. The resulting milky solution was extracted with EtOAc. The ethyl acetate extract was dried over $MgSO_4$ and filtered. Solvent removal gave a white solid. The solid was purified by crystalization from diethyl ether and hexane. The desired acid was obtained in 78% yield.

$^1$H NMR (CDCl$_3$) δ12.71 (s, 1), 7.43 (s, 1), 7.07 (t, 1, J=8.28 Hz), 6.58 (d, 1, J=8.28 Hz), 6.42 (s, 1), 6.41 (d, 1, J=8.28 Hz), 4.77 (q, 1, J=6.84 Hz), 4.23 (t, 2, J=6.00 Hz), 4.17 (t, 2, J=5.96 Hz), 2.67 (m, 2), 2.58 (s, 3), 2.56 (m, 2), 2.33 (m, 2), 1.66 (d, 3, J=6.80 Hz), 1.53 (m, 2), 1.77 (t, 3, J=7.47 Hz), 0.93 (t, 3, J=7.31 Hz) IR (CHCl$_3$) 2966, 2930, 2860, 1748, 1715, 1633, 1593 cm$^{-1}$ Mass Spec (FD) (m/z) 444 (M$^+$)

Elem Anal Calc'd for $C_{25}H_{33}O_7$: C, 67.56; H, 7.26 Found: C, 67.43; H, 7.33

EXAMPLE 5

Preparation of 2-[3-[3-(4-acetyl-2-ethyl-5-hydroxyphenoxy)propoxy)-2-propylphenoxy]butanoic acid.

A. Ethyl 2[2-propyl-3-hydroxyphenoxy]butyrate.

Sodium hydride (0.97 g of a 60% oil dispersion, 24 mmol) under argon arm was washed with 15 mL of dry hexane. The hexane supernatant was removed via syringe. Dry THF (40 mL) was added to the NaH and with stirring at room temperature, the dihydroxypropylbenzene (3.68 g, 24 mmol) was added as a 40 mL THF solution. After stirring at room temperature for 25 minutes, the ethyl 2-bromo-proprionate (4.48 g, 23 mmol) was added rapidly. After stirring at room temperature for 17 hours, the reaction was quenched with saturated aqueous $NH_4Cl$ solution, and the THF was removed under vacuum. The resulting aqueous mixture was extracted several times with EtOAc. The organic extract was dried over $MgSO_4$. Filtration and solvent removal gave an orange oil. This oil was purified by Waters Prep 500 chromatography on silica gel eluting with 5 to 30% EtOAc/Hexane gradient. The desired product was obtained as a clear oil (2.10 g, 33%).

TLC Rf=0.39 (30% EtOAc/Hexane, Silica gel) $^1$H NMR (CDCl$_3$) δ6.96 (t, 1, J=8.2 Hz), 6.45 (d, 1, J=8.12 Hz), 6.28 (d, 1, J=8.12 Hz), 4.88 (s, 1), 4.59 (t, 1, J=6.04 Hz), 4.20 (q, 2, J=7.52 Hz), 2.69 (m, 2), 2.02 (m, 2), 1.63 (m, 2), 1.24 (t, 3, J=7.03 Hz), 1.10 (t, 3, J=7.43 Hz), 0.99 (t, 3, J=7.40 Hz) IR (CHCl$_3$) 3603, 3009, 2966, 2936, 2873, 1748, 1728, 1596 cm$^{-1}$ Mass Spec (FAB) (m/z) 267 (M$^+$+H), 266 (M$^+$)

B. Ethyl 2-[2-propyl-3-(3-chloropropyloxy)phenoxy]butyrate.

A solution (0.3M) of ethyl 2[2-propyl-3-hydroxyphenoxy]butyrate in dry DMF was stirred under argon atmosphere and at room temperature with solid $K_2CO_3$ (1.75 eqv). To this suspension added 1-bromo-2-chloropropane (2.5 eqv.). The reaction was stirred at room temperature fro 20 hours and then quenched with water. The reaction mixture was extracted with EtOAc (three times), and the ethyl acetate extract was washed with water and then dried over $MgSO_4$. Filtration and solvent removal gave the crude product as an oil which was purified by flash chromatography on silica gel eluting with 15% EtOAc/Hexane. Ethyl 2-[2-propyl-3-(3-chloropropyloxy)-phenoxy]butyrate was prepared in 85% yield.

$^1$H NMR (CDCl$_3$) δ7.05(t, 1, J=8.26 Hz), 6.55 (d, 1, J=8.18 Hz), 6.35 (d, 1, J=8.27 Hz), 4.60 (t, 1, J=6.02 Hz), 4.20 (q, 2, J=7.13 Hz), 4.11 (t, 2, J=5.75 Hz), 3.79 (t, 2, J=6.36 Hz), 2.72 (m, 2), 2.26 (m, 2), 2.01 (m, 2), 1.59 (m, 2), 1.25 (t, 3, J=7.18 Hz), 1.11 (t, 3, J=7.39 Hz), 0.97 (t, 3, J=7.35 Hz) IR (CHCl$_3$) 3020, 2967, 2935, 2872, 1749, 1727, 1594 cm$^{-1}$ Mass Spec (FAB) (m/z) 343 (M$^+$+H), 342 (M+)

Elem Anal Calc'd for $C_{18}H_{27}O_4Cl$: C, 63.06; H, 7.94; Cl, 10.34 Found: C, 63.19; H, 7.84; Cl, 10.58

C. Ethyl 2-[3-[3-(4-acetyl-2-ethyl-5-hydroxyphenoxy)propoxy)-2-propylphenoxy]butanoate.

To a solution of 2,4-dihydroxy-4-ethyl acetophenone in 5:1 methylethylketone and DMSO (0.45M soln) at room temperature added ethyl 2-[2-propyl-3-(3-chloropropyloxy)phenoxy]butyrate (1.0 eqv), $K_2CO_3$ (1.75 eqv) and KI (0.20 eqv). The reaction was then refluxed for 20 hours. The reaction was then cooled to room temperature and quenched with water. The reaction mixture was extracted with EtOAc (three times) and this extract was washed with water and then dried over MgSO$_4$. Filtration and solvent removal gave a crude product which was purified by flash chromatography on silica gel eluting with 20% EtOAc/Hexane. Ethyl 2-[3-[3-(4-acetyl-2-ethyl-5-hydroxyphenoxy)propoxy)- 2-propylphenoxy]butanoate was prepared in 78% yield.

$^1$H NMR (CDCl$_3$) δ12.72 (s, 1), 7.43 (s, 1), 7.04 (t, 1, J=8.29 Hz), 6.55 (d, 1, J=8.30 Hz), 6.42 (s, 1), 6.34 (d, 1, J=8.30 Hz), 4.58 (t, 1, J=5.98 Hz), 4.20 (m, 6), 2.72 (m, 2), 2.57 (s, 3), 2.56 (m, 2), 2.32 (m, 2), 2.01 (m, 2), 1.53 (m, 2), 1.23 (t, 3, J=7.06 Hz), 1.18 (t, 3, J=7.45 Hz), 1.10 (t, 3, J=7.38 Hz), 0.94 (t, 3, J=7.33 Hz). IR (CHCl$_3$) 2969, 2931, 1754, 1730, 1633, 1595 cm$^{-1}$ Mass Spec (FD) (m/z) 486 (M$^+$)

Elem Anal Calc'd for C$_{28}$H$_{38}$O$_7$: C, 69.11; H, 7.87 Found: C, 69.08, H, 8.05

D.  2-[3-[3-(4-acetyl-2-ethyl-5-hydroxyphenoxy)propoxy)-2-propylphenoxy]butanoic acid.

A solution of ethyl 2-[2-propyl-3-[[3-(4-acetyl-2-ethyl-5-hydroxy-phenoxy)propyl]oxy]phenoxy]butanoate in dioxane (3.5M solution) was treated with 2N NaOH (3.0 eqv) and stirred at room temperature. After stirring for 4 hours, the dioxane was removed from the reaction, and the remaining solution was diluted with water and acidified with 5N HCl. The resulting milky solution was extracted with EtOAc. The ethyl acetate extract was dried over MgSO$_4$ and filtered. Solvent removal gave a white solid. The solid was purified by crystalization from diethylether and hexane. The desired acid was obtained in 69% yield.

$^1$H NMR (CDCl$_3$) δ12.72 (s, 1), 7.43 (s, 1), 7.07 (t, 1, J=8.28 Hz), 6.58 (d, 1, J=8.28 Hz), 6.48 (s, 1), 6.38 (d, 1, J=8.28 Hz), 4.63 (t, 1, J=5.98 Hz), 4.23 (t, 2, J=6.00 Hz), 4.17 (t, 2, J=5.98 Hz), 2 .68 (m, 2), 2.58 (s, 3), 2.56 (m, 2), 2.33 (m, 2), 2.05 (m, 2), 1.54 (m, 2), 1.18 (t, 3, J=7.42 Hz), 1.12 (t, 3, J=7.36 Hz), 0.94 (t, 3, J=7.29 Hz) IR (KBr) 2966, 2930, 2871, 1705, 1641, 1593 cm$^{-1}$ Mass Spec (FD) (m/z) 458 (M$^+$)

Elem Anal Calc'd for C$_{26}$H$_{34}$O$_7$: C, 68.10; H, 7.47 Found: C, 68.01; H, 7.51

EXAMPLE 6

Preparation of
6-iodo-8-propyl-7-[3-[4-acetyl-2-ethyl-5-hydroxyphenoxy)propoxy]-
3,4-dihydro-2H-1-benzopyran-2-caroxylic acid.

A. 6-iodo-8-propyl-7-[3-[4-acetyl-2-ethyl-5-hydroxyphenoxy)propoxy]-3,4-dihydro- 2H-1-benzopyran-2-caroxylic acid.

7-[3-(4-acetyl-2-ethyl-5-hydroxyphenoxy)propoxy]-3,4-dihydro- 8-propyl-2H-1-benzopyran-2-carboxylic acid (150 mg) was dissolved in acetic acid. To this solution added AgOAc (55 mg) followed by iodine (85 mg). The reaction was stirred for 4 hours. The reaction was quenched with water and extracted with EtOAc. The acetic acid was removed by a toluene azeotrope. Solvent removal gave the desired iodide (140 mg, 73%).

$^1$H NMR (CDCl$_3$) δ7.47 (s, 1), 7.33 (s, 1), 6.47 (s, 1), 4.80 (m, 1), 4.33 (t, 2, J=6.00 Hz), 4.04 (t, 2, J=6.00 Hz), 4.53 (s, 1), 2.73 (m, 2), 2.61 (m, 2), 2.60 (s, 3), 2.53 (m, 2), 2.23 (m, 2), 2.56 (m, 2), 1.24 (t, 3, J=7.40 Hz), 0.88 (t, 3, J=7.30 Hz)

Elem Anal Calc'd for C$_{26}$H$_{31}$O$_7$I: C, 53.62; H, 5.36 Found: C, 53.90; H, 5.60

EXAMPLE 7

Preparation of
6-[3-(4-acetyl-2-ethyl-5-hydroxyphenoxy)propoxy]-
9-oxo-9H-xanthene- 2-carboxylic acid disodium salt sesquihydrate

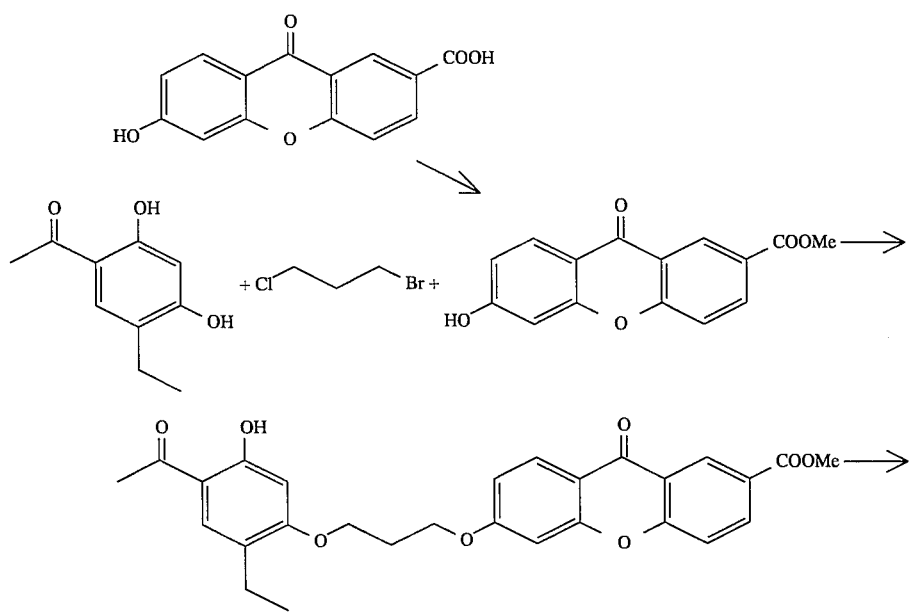

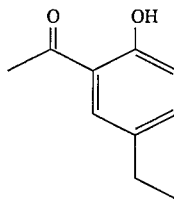

A. 6-Hydroxy-9-oxo-9H-xanthene-2-carboxylic acid methyl ester.

A mixture of 6-hydroxy-9-oxo-9H-xanthene-2-carboxylic acid (Gapinski, D. M. "Leukotriene Antagonists", U.S. Pat. No. 4,996,230, which is incorporated herein by reference, 1991; 10.6 g, 41.4 mmol) and concentrated sulfuric acid (1 mL) in methanol (100 mL) was refluxed for 48 hours. The mixture was cooled to room temperature and the resulting precipitate collected by vacuum filtration. The filtrate was concentrated in vacuo and diluted with water, which resulted in additional precipitate. This was collected and combined with the first fraction to provide 10.8 g (97%) of the title product:

$^1$H-NMR (DMSO-$d_6$) 11.03 (s, 1H, —OH), 8.56 (d, J=2 Hz, 1H), 8.18 (dd, J=9, 2 Hz, 1H), 7.96 (d, J=9 Hz, 1H), 7.59 (d, J=9 Hz, 1H), 6.88 (dd, J=9, 2 Hz, 1H), 6.81 (d, J=2 Hz, 1H), 3.86 (s, 3H); MS-FAB (m/e) 271 (p+1, 6); IR (KBr, cm$^{-1}$) 3093 (b), 1727, 1604, 1459, 1282, 1120, 767. Anal. ($C_{15}H_{10}O_5$:

|  | C | H |
|---|---|---|
| Theory | 66.67 | 3.73 |
| Found | 66.09 | 3.96 |

B. 6-[3-(4-Acetyl-2-ethyl-5-hydroxyphenoxy)propoxy]-9-oxo-9H-xanthene-2-carboxylic acid methyl ester.

A mixture of 6-hydroxy-9-oxo-9H-xanthene-2-carboxylic acid methyl ester (750 mg, 2.78 mmol), 1-bromo-3-chloropropane (482 mg, 30.6 mmol), potassium carbonate (1.15 g, 8.33 mmol), potassium iodide (46 mg, 0.28 mmol), and dimthylsulfoxide (3 mL) was refluxed in 2-butanone (11 mL) for 1 hour. The mixture was cooled to room temperature and 2,4-dihydroxy-5-ethylacetophenone (500 mg, 2.78 mmol) added. The resulting mixture was refluxed for 18 hours, cooled to room temperature, and diluted with ethyl acetate. This mixture was washed once with water and once with saturated sodium chloride solution. The organic layer was dried (sodium sulfate), filtered, and concentrated in vacuo to profide a brown solid. Chromatography (hexane/ethyl acetate) provided 0.88 g (64%) of the title product as a colorless oil:

$^1$H-NMR (CDCl$_3$) 12.71 (s, 1H, —OH), 9.02 (d, J=2.2 Hz, 1H), 8.36 (dd, J=9, 2 Hz, 1H), 7.51 (d, J=9 Hz, 1H), 7.44 (s, 1H), 7.00 (dd, J=9, 2 Hz, 1H), 6.94 (d, J=2 Hz, 1H), 6.44 (s, 1H), 4.33, (t, J=6 Hz, 2H), 4.25 (t, J=6 Hz, 2H), 3.99 (s, 3H), 2.57 (m, 5H), 2.41 (quintet, J=6 Hz, 2H), 1.20 (t, J=5 Hz, 3H).

C. 6-[3-(4-Acetyl-2-ethyl-5-hydroxyphenoxy)propoxy]-9-oxo-9H-xanthene-2-carboxylic acid disodium salt sesquihydrate.

A mixture of 6-[3-(4-acetyl-2-ethyl-5-hydroxyphenoxy)propoxy]-9-oxo-9H-xanthene- 2-carboxylic acid methyl ester (380 mg) and 5N aqueous sodium hydroxide solution (4 mL) in 1:1 methanol/tetrahydrofuran (20 mL) was stirred at room temperature for 24 hours. The mixture was acidified with aqueous 5N hydrochloric acid solution and the resulting precipitate was collected via vacuum filtration. This material was dissolved in a minimum of aqueous 1N sodium hydroxide solution and purified on MCI HP-20™ resin using a water/acetonitrile gradient. Lyophilization of the appropriate fractions provided 120 mg (35%) of the title product as a fluffy white solid: $^1$H-NMR (DMSO-$d_6$) 8.64 (d, J=2 Hz, 1H), 8.27 (dd, J=9, 2 Hz, 1H), 8.05 (d, J=9 Hz, 1H), 7.59 (s, 1H), 7.44 (d, J=9 Hz, 1H), 7.13 (d, J=2 Hz, 1H), 7.01 (dd, J=9, 2 Hz, 1H), 6.54 (s, 1H), 4.32 (t, J=5 Hz, 2H), 4.21 (t, J=6 Hz, 2H), 2.51 (m, 5H), 2.25 (quintet, J=5 Hz, 2H), 1.10 (t, J=8 Hz, 3H); MS-FAB (m/e) 521 (p+1, 35), 500 (22), 499 (63), 477 (18); IR (CHCl$_3$, cm$^{-1}$) 3450 (b), 2976, 1620, 1401, 1268, 1162, 1049. Anal. ($C_{27}H_{22}O_8Na_2 \cdot 1.5\ H_2O$):

|  | C | H |
|---|---|---|
| Theory | 59.23 | 4.05 |
| Found | 59.54 | 4.39 |

EXAMPLE 8

Preparation of 3-[1-[2-[3-(4-acetyl-2-ethyl-5-hydroxyphenoxy)propoxy]dibenzofuran]]propanoic acid disodium salt

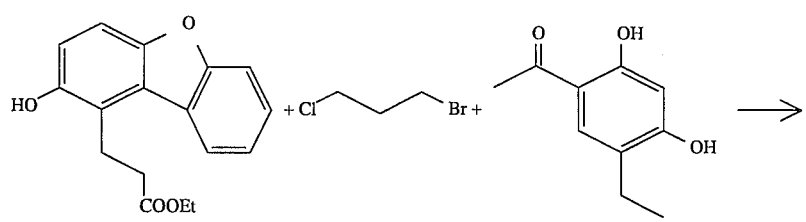

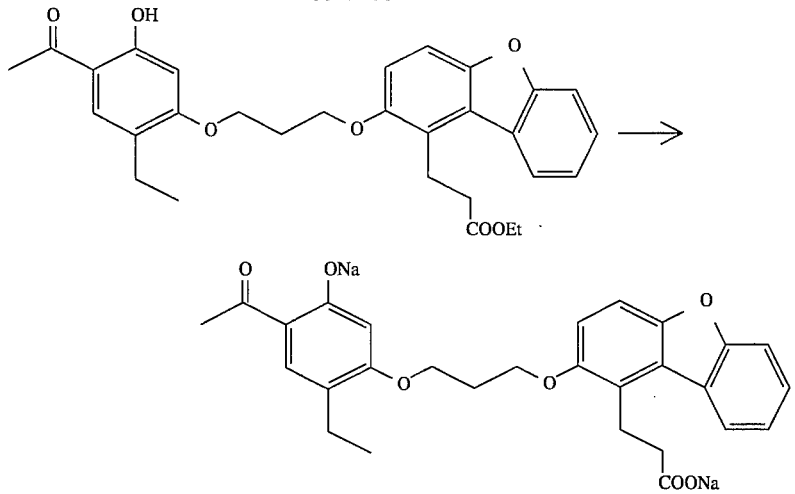

A. 3-[1-[2-[3-(4-Acetyl-2-ethyl-5-hydroxyphenoxy)propoxy]dibenzofuran]]propanoic acid ethyl ester.

A solution of 3-[1-(2-hydroxydibenzofuran)]propanoic acid ethyl ester (1.00 g, 3.52 mmol) in dimethylformamide (10 mL) was carefully treated with 97% sodium hydride (93.0 mg, 3.87 mmol) at room temperature. After stirring for 30 minutes, 1-bromo-3-chloropropane(610 mg, 3.87 mmol) was added and the resulting mixture stirred at room temperature for 18 hours. The mixture was diluted with ether and washed once with water and once with aqueous 1N sodium hydroxide solution. The organic layer was dried (sodium sulfate), filtered and concentrated in vacuo to provide an orange oil. A mixture of this material and 2,4-dihydroxy-5-ethylacetophenone (530 mg, 2.94 mmol), potassium carbonate (1.22 g, 8.82 mmol), potassium iodide (48 mg, 0.29 mmol), and dimethylsulfoxide (5 mL) in 2-butanone (15 mL) was refluxed for 5 hours. The mixture was cooled to room temperature and diluted with ether. The resulting mixture was washed once with saturated sodium chloride solution and once with aqueous 1N sodium hydroxide solution. The organic layer was dried (sodium sulfate), filtered, and concentrated in vacuo to provide a brown oil. Purification via silica gel chromatography (hexane/ethyl acetate) provided 855 mg (48%) of the title product as a colorless oil:

$^1$H-NMR (CDCl$_3$) 12.71 (s, 1H, —OH), 8.10 (d, J=8 Hz, 1H), 7.56 (d, J=8 Hz, 1H), 7.48 (d, J=7 Hz, 1H), 7.44 (s, 1H), 7.38 (m, 2H), 7.05 (d, J=9 Hz, 1H), 6.46 (s, 1H), 4.30 (t, J=6 Hz, 2H), 4.26 (t, J=5 Hz, 2H), 4.18 (q, J=7 Hz, 2H), 3.48 (t, J=8 Hz, 2H), 2.68 (t, J=6 Hz, 2H), 2.57 (m, 5H), 2.40 (quintet, J=6 Hz, 2H), 1.26 (t, J=7 Hz, 3H), 1.81 (t, J=7 Hz, 3H).

B. 3-[1-[2-[3-(4-Acetyl-2-ethyl-5-hydroxyphenoxy)propoxy]dibenzofuran]]propanoic acid disodium salt.

Hydrolysis of 855 mg of 3-[1-[2-[3-(4-acetyl-2-ethyl-5-hydroxyphenoxy)propoxy]dibenzofuran]]propanoic acid ethyl ester followed by sodium salt formation and purification as described above in Example 1C provided 595 mg (67%) of the title product as a fluffy white solid:

$^1$H-NMR (DMSO-d$_6$) 8.18 (d, J=9 Hz, 1H), 7.63 (d, J=8 Hz, 1H), 7.47 (m, 2H), 7.41 (d, J=9 Hz, 1H), 7.36 (t, J=8 Hz, 1H), 7.13 (d, J=9 Hz, 1H), 6.72 (s, 1H), 4.28 (t, J=7 Hz, 2H), 4.15 (t, J=6 Hz, 2H), 3.32 (m, 2H), 2.47 (m, 5H), 2.22 (m, 4H), 1.07 (t, J=7 Hz, 3H); MS-FAB (m/e) 521 (p+1, 32), 500 (36), 499 (100), 477 (35); IR (KBr, cm$^{-1}$) 3430 (b), 2927, 1634, 1567, 1427, 1372, 1255, 1162. Anal. (C$_{28}$H$_{26}$O$_7$Na$_2$):

|         | C     | H    |
|---------|-------|------|
| Theory  | 64.61 | 5.03 |
| Found   | 64.37 | 5.27 |

EXAMPLE 9

Preparation of 3-[3-propyl-4-[3-(4-acetyl-2-ethyl-5-hydroxyphenoxy)propoxy]phenoxy]benzoic acid disodium salt

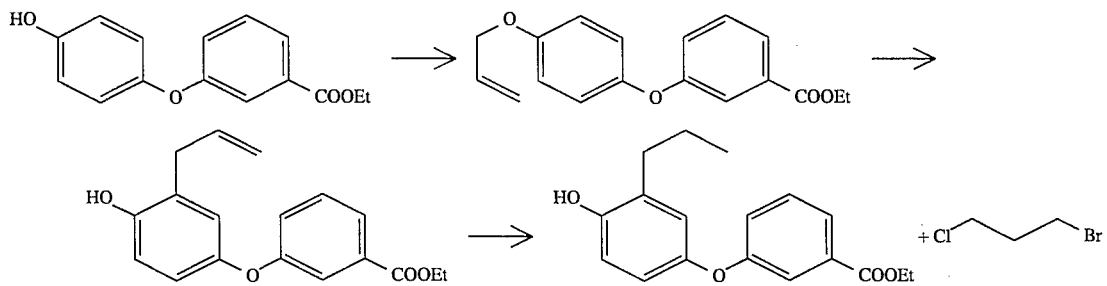

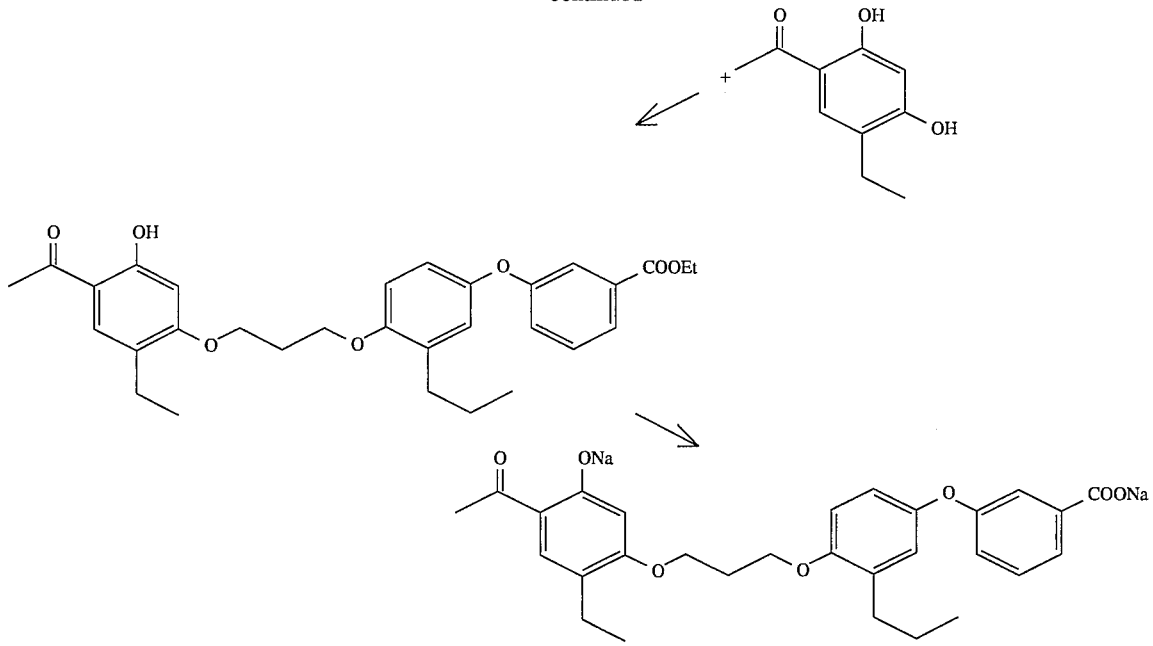

A. 3-(4-Hydroxy-3-propylphenoxy)benzoic acid ethyl ester.

To a solution of 3-(3-allyl-4-hydroxyphenoxy)benzoic acid ethyl ester (Gapinski, D. M.; Mallet, B. E.; Froelich, L. L.; Jackson, W. T., J. Med. Chem., 33, 2798–2813 (1990) incorporated herein by reference; 2.45 g) in methanol (15 mL) was added 10% palladium-on-carbon (300 mg). Hydrogen was bubbled through the resulting suspension for 5 minutes. The mixture was placed under 1 atm of hydrogen with stirring for 48 hours at room temperature. The mixture was de-gassed with nitrogen, filtered, and concentrated in vacuo to give 2.38 g (96%) of the title product as a colorless oil:

$^1$H-NMR (CDCl$_3$) 7.74 (d, J=8 Hz, 1H), 7.64 (d, J=2 Hz, 1H), 7.37 (t, J=8 Hz, 1H), 7.15 (dd, J=9, 2 Hz, 1H), 6.86 (dd, J=2 Hz, 1H), 6.78 (m, 2H), 5.14 (bs, 1H, —OH), 4.38 (q, J=7 Hz, 2H), 2.59 (t, J=7 Hz, 2H), 1.65 (hextet, J=8 Hz, 2H), 1.39 (t, J=7 Hz, 3H), 0.98 (t, J=7 Hz, 3H).

B. 3-[3-Propyl-4-[3-(4-acetyl-2-ethyl-5-hydroxyphenoxy)propoxy]phenoxy]benzoic acid ethyl ester.

3-(4-Hydroxy-3-propylphenoxy)benzoic acid ethyl ester (680 mg, 2.27 mmol) was alkylated with 1-bromo-3-chloropropane followed by 2,4-dihydroxy-5-ethylacetophenone as described above in Example 2A to provide a brown oil. Silica gel chromatography (hexane/ethyl acetate) provided 532 mg (45%) of the title product as a colorless oil:

$^1$H-NMR (CDCl$_3$) 12.73 (s, 1H, —OH), 7.73 (d, J=8 Hz, 1H), 7.63 (s, 1H), 7.44 (s, 1H), 7.36 (t, J=8 Hz, 1H), 7.14 (dd, J=9, 2 Hz, 1H), 6.85 (m, 3H), 6.44 (s, 1H), 4.36 (q, J=7 Hz, 2H), 4.25 (t, J=6 Hz, 2H), 4.18 (t, J=6 Hz, 2H), 2.58 (m, 7H), 2.35 (quintet, J=6 Hz, 2H), 1.59 (hextet, J=8 Hz, 2H), 1.38 (t, J=7 Hz, 3H), 1.19 (t, J=7 Hz, 3H), 0.93 (t, J=7 Hz, 3H); MS-FD (m/e) 520 (p); IR (CHCl$_3$, cm$^{-1}$) 3490 (b), 2967, 1717, 1634, 1497, 1372, 1271, 1073. Anal. (C$_{31}$H$_{36}$O$_7$):

|  | C | H |
|---|---|---|
| Theory | 71.51 | 6.97 |
| Found | 71.23 | 6.80 |

C. 3-[3-Propyl-4-[3-(4-acetyl-2-ethyl-5-hydroxyphenoxy)propoxy]phenoxy]benzoic acid disodium salt.

Hydrolysis of 512 mg of 3-[3-propyl-4-[3-(4-acetyl-2-ethyl- 5-hydroxyphenoxy)propoxy]phenoxy]benzoic acid ethyl ester followed by sodium salt formation and purification as described above in Example 1C provided 267 mg (51%) of the title product as a fluffy white solid:

$^1$H-NMR (DMSO-d$_6$) 7.59 (s, 1H), 7.51 (d, J=8 Hz, 1H), 7.31 (s, 1H), 7.19 (t, J=8 Hz, 1H), 6.95 (d, J=8 Hz, 1H), 6.83 (d, J=8 Hz, 1H), 6.77 (m, 2H), 6.51 (s, 1H), 4.20 (t, J=6 Hz, 2H), 4.12 (t, J=6 Hz, 2H), 2.53 (s, 3H), 2.44 (m, 4H), 2.20 (quintet, J=6 Hz, 2H), 1.45 (hextet, J=7 Hz, 2H), 1.07 (t, J=7 Hz, 3H), 0.80 (t, J=7 Hz, 3H); MS-FAB (m/e) 537 (p+1, 100), 515 (82); IR (CHCl$_3$, cm$^{-1}$) 2967, 1634, 1561, 1497, 1269, 1162, 1071. Anal. (C$_{29}$H$_{30}$O$_7$Na$_2$):

|  | C | H |
|---|---|---|
| Theory | 67.63 | 5.88 |
| Found | 67.90 | 6.02 |

EXAMPLE 10

Preparation of 4-[3-propyl-4-[3-(4-acetyl-2-ethyl-5-hydroxyphenoxy)propoxy]phenoxy]benzoic acid sodium salt hydrate

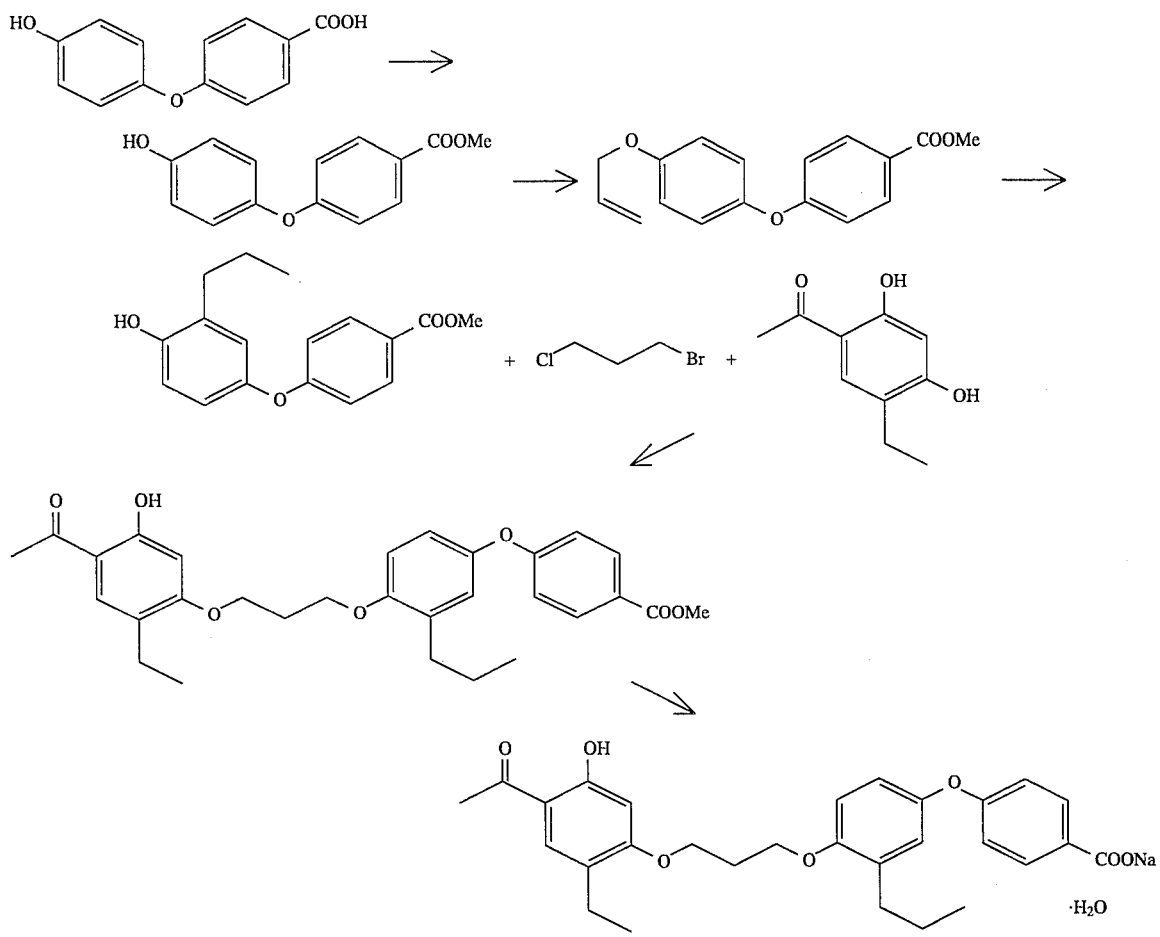

A. 4-(4-Hydroxyphenoxy)benzoic acid methyl ester.

A mixture of 4-(4-hydroxyphenoxy)benzoic acid (20.0 g, 87.0 mmol) and concentrated sulfuric acid (5 mL) was refluxed for 48 hours. The mixture was cooled to room temperature and the resulting precipitate was collected via vacuum filtration to give 20.5 g (97%) of the title product as a white crystalline material:

mp 130°–134° C.; $^1$H-NMR (CDCl$_3$) 9.30 (bs, 1H, —OH), 7.89 (d, J=9 Hz, 2H), 6.92 (m, 4H), 6.80 (d, J=9 Hz, 2H), 3.79 (s, 3H); MS-EI (m/e) 245 (p+1, 45), 244 (p, 100), 214 (30), 213 (100), 157 (32); IR (CHCl$_3$, cm$^{-1}$) 3350 (b), 1715, 1605, 1501, 1437, 1284, 1239, 1194. Anal. (C$_{14}$H$_{12}$O$_4$):

|  | C | H |
|---|---|---|
| Theory | 68.85 | 4.95 |
| Found | 69.20 | 4.94 |

B. 4-(4-Allyloxyphenoxy)benzoic acid methyl ester.

A mixture of 4-(4-hydroxyphenoxy)benzoic acid methyl ester (5.00 g, 20.5 mmol), allyl iodide (3.79 g, 22.5 mmol), potassium carbonate (8.49 g, 61.5 mmol), and dimethylsulfoxide (10 mL) in 2-butanone (40 mL) was refluxed for 24 hours. The mixture was cooled to room temperature and diluted with ether. The resulting mixture was washed once with water and once with saturated sodium bicarbonate solution. The organic layer was dried (sodium sulfate), filtered, and concentrated in vacuo to provide 4.52 g (78%) of the title intermediate as a white solid:

mp 75° C.; $^1$H-NMR (CDCl$_3$) 7.99 (d, J=9 Hz, 2H), 7.03 (d, J=9 Hz, 2H), 6.95 (m, 4H), 6.08 (m, 1H), 5.46 (d, J=14 Hz, 1H), 5.31 (d, J=10 Hz, 1H), 4.55 (d, J=7 Hz, 2H), 3.92 (s, 3H).

C. 4-(4-Hydroxy-3-propylphenoxy)benzoic acid methyl ester.

4-(4-Allyloxyphenoxy)benzoic acid methyl ester (4.98 g) was heated to 225° C. for 7 hours. This material was hydrogenated as described above in Example 3A to provide 3.49 g (70%) of the title intermediate as a colorless oil:

$^1$H-NMR (CDCl$_3$) 8.00 (d, J=9 Hz, 2H), 6.94 (d, J=9 Hz, 2H), 6.90–6.77 (m, 3H), 5.37 (bs, 1H, —OH), 3.92 (s, 3H), 2.60 (t, J=7 Hz, 2H), 1.66 (hextet, J=8 Hz, 2H), 0.98 (t, J=7 Hz, 3H); MS-FAB (m/e) 287 (p+1, 100), 286 (p, 94), 257 (22), 255 (42); IR (CHCl$_3$, cm$^{-1}$) 3450 (b), 2950, 1715, 1510, 1500, 1437, 1284, 1240, 1164. Anal. (C$_{17}$H$_{18}$O$_4$):

|  | C | H |
|---|---|---|
| Theory | 71.31 | 6.34 |
| Found | 71.03 | 6.20 |

D. 4-[3-Propyl-4-[3-(4-acetyl-2-ethyl-5-hydroxyphenoxy)propoxy]phenoxy]benzoic acid methyl ester.

4-(4-Hydroxy-3-propylphenoxy)benzoic acid methyl ester (1.50 g, 5.24 mmol) was alkylated with 1-bromo-3-chloropropane as described above in Example 2A. The resulting material was dissolved in hexane and passed down a short silica gel column. Concentration in vacuo provided a colorless oil which was further alkylated with 2,4-dihydroxy-5-ethylacetophenone as described in Example 2A to provide 455 mg (17%) of the title intermediate as a colorless oil:

$^1$H-NMR (CDCl$_3$) 7.98 (d, J=9 Hz, 2H), 7.45 (s, 1H), 6.93 (d, J=9 Hz, 2H), 6.87 (m, 3H), 6.44 (s, 1H), 4.25 (t, J=6 Hz, 2H), 4.19 (t, J=6 Hz, 2H), 3.90 (s, 3H), 2.58 (m, 7H), 2.38 (quintet, J=6 Hz, 2H), 1.59 (hextet, J=8 Hz, 2H), 1.18 (t, J=8 Hz, 3H), 0.93 (t, J=7 Hz, 3H).

E. 4-[3-Propyl-4-[3-(4-acetyl-2-ethyl-5-hydroxyphenoxy)propoxy]phenoxy]benzoic acid sodium salt hydrate.

Hydrolysis of 455 mg of 4-[3-propyl-4-[3-(4-acetyl-2ethyl- 5-hydroxyphenoxy)propoxy]phenoxy]benzoic acid methyl ester followed by sodium salt formation and purification as described above in Example 1C provided 161 mg (35%) of the title product as a fluffy white solid:

$^1$H-NMR (DMSO-d$_6$) 7.80 (d, J=9 Hz, 2H), 7.59 (s, 1H), 6.95 (d, J=9 Hz, 1H), 6.78 (m, 2H), 6.74 (d, J=9 Hz, 2H), 6.53 (s, 1H), 4.21 (t, J=6 Hz, 2H), 4.11 (t, J=6 Hz, 2H), 2.53 (s, 3H), 2.48 (m, 4H), 2.20 (quintet, J=6 Hz, 2H), 1.45 (hextet, J=7 Hz, 2H), 1.06 (t, J=7 Hz, 3H), 0.79 (t, J=7 Hz, 3H); MS-FAB (m/e) 515 (p+1, 33), 493 (41), 494 (43), 476 (33), 475 (100); IR (CHCl$_3$, cm$^{-1}$) 2964, 1635, 1601, 1497, 1417, 1270, 1163. Anal. (C$_{29}$H$_{31}$O$_7$Na . H$_2$O):

|  | C | H |
| --- | --- | --- |
| Theory | 65.47 | 6.02 |
| Found | 65.68 | 5.91 |

EXAMPLE 11

Preparation of 3-[1-[5-phenyl-2-[3-(4-acetyl-2-ethyl-5-hydroxyphenoxy)propoxy]phenyl]]propanoic acid disodium salt,

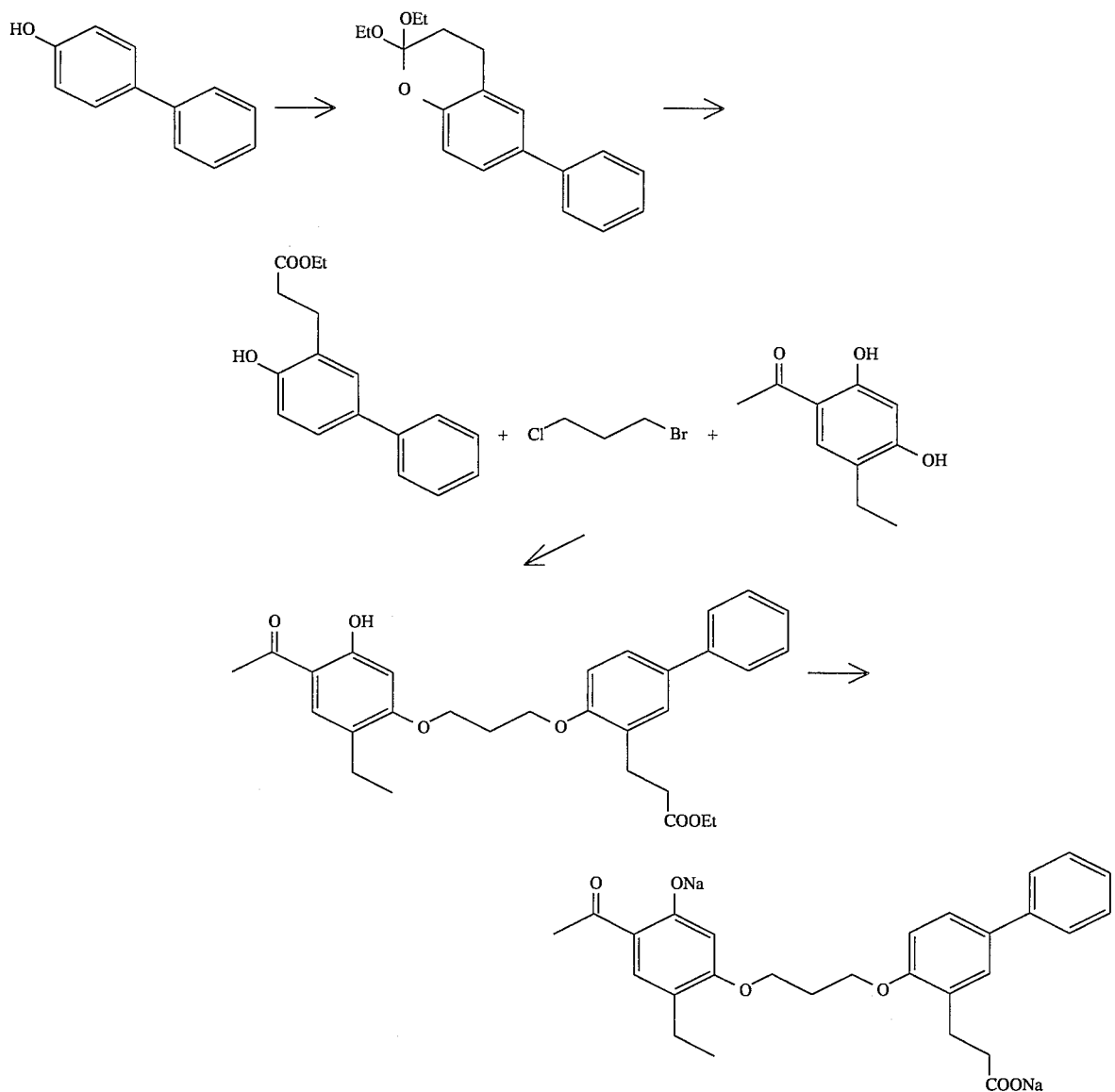

A. 2,2-Diethoxy-3,4-dihydro-6-phenyl-2H-1-benzopyran.

A mixture of 4-phenylphenol (5.00 g, 29.4 mmol), triethylorthoacrylate (10.9 g, 58.8 mmol), and pivalic acid (1.50 g, 14.7 mmol) in toluene (100 mL) was refluxed for 42 hours. The mixture was cooled to room temperature and diluted with ether. The resulting solution was washed once with water and once with saturated sodium bicarbonate solution. The organic layer was dried (sodium sulfate), filtered, and concentrated in vacuo to provide a colorless oil. Crystallization from hexane provided 8.08 g (92%) of the title intermediate as a white crystalline material:

mp 91° C.; $^1$H-NMR (CDCl$_3$) 7.57 (d, J=7 Hz, 2H), 7.25–7.50 (m, 5H), 6.98 (d, J=8 Hz, 1H), 3.87 (m, 4H), 2.96 (t, J=7 Hz, 2H), 2.16 (t, J=7 Hz, 2H), 1.25 (t, J=7 Hz, 6H); MS-FD (m/e) 299 (p+1, 44), 298 (100), 270 (24); IR (CHCl$_3$, cm$^{-1}$) 2982, 1483, 1096, 1069, 972. Anal. (C$_{19}$H$_{22}$O$_3$):

|  | C | H |
|---|---|---|
| Theory | 76.48 | 7.43 |
| Found | 76.52 | 7.39 |

B. 3-[1-[(2-Hydroxy-5-phenyl)phenyl]]propanoic acid ethyl ester.

A mixture of 2,2-diethoxy-3,4-dihydro-6-phenyl-2H-1-benzopyran (2.50 g) and aqueous 5N hydrochloric acid (0.25 mL) in tetrahydrofuran (25 mL) was stirred at room temperature for 5 minutes. The mixture was diluted with ether and washed once with water and once with saturated sodium bicarbonate solution. The organic layer was dried (sodium sulfate), filtered, and concentrated in vacuo to provide 2.10 g (93%) of the title intermediate as a white solid:

mp 35°–39° C.; $^1$H-NMR (CDCl$_3$) 7.55 (d, J=8 Hz, 2H), 7.25–7.50 (m, 5H), 6.99 (d, J=8 Hz, 1H), 4.18 (q, J=7 Hz, 2H), 2.99 (t, J=6 Hz, 2H), 2.81 (t, J=5 Hz, 2H), 1.27 (t, J=8 Hz, 3H); MS-FD (m/e) 271 (p+1, 42), 270 (p, 100); IR (CHCl$_3$, cm$^{-1}$) 3350 (b), 3012, 1708, 1485, 1379, 1165. Anal. (C$_{17}$H$_{18}$O$_3$):

|  | C | H |
|---|---|---|
| Theory | 75.53 | 6.71 |
| Found | 77.70 | 6.77 |

C. 3-[1-[5-Phenyl-2-[3-(4-acetyl-2-ethyl- 5hydroxyphenoxy)propoxy]-phenyl]]propanoic acid ethyl ester.

3-[1-[(2-Hydroxy-5-phenyl)phenyl]]propanoic acid ethyl ester (1.11 g, 4.10 mmol) was alkylated with 1-bromo-3-chloropropane followed by 2,4-dihydroxy-5-ethylacetophenone as described in Example 2A to provide a brown oil. Silica gel chromatography (hexane/ethyl acetate) provided 1.11 g (55%) of the title intermediate as a white microcrystalline solid:

mp 75° C.; $^1$H-NMR (CDCl$_3$) 12.71 (s, 1H, —OH), 7.55 (d, J=7 Hz, 2H), 7.43 (m, 5H), 7.30 (t, J=7 Hz, 1H), 6.94 (d, J=9 Hz, 1H), 6.44 (s, 1H), 4.25 (m, 4H), 4.14 (q, J = 7 Hz, 2H), 3.02 (t, J=8 Hz, 2H), 2.50–2.70 (m, 7H), 2.38 (quintet, J=6 Hz, 2H), 1.24 (t, J=7 Hz, 3H), 1.19 (t, J=8 Hz, 3H); MS-FD (m/e) 491 (p+1, 35), 490 (100); IR (CHCl$_3$, cm$^{-1}$) 3400 (b) , 2980, 1740, 1634, 1373, 1269, 1245, 1162. Anal. (C$_{30}$H$_{34}$O$_6$):

|  | C | H |
|---|---|---|
| Theory | 73.45 | 6.99 |
| Found | 73.21 | 7.24 |

D. 3-[1-[5-Phenyl-2-[3-(4-acetyl-2-ethyl- 5hydroxyphenoxy)propoxy]phenyl]]propanoic acid disodium salt.

Hydrolysis of 1.08 g of 3-[1-[5-phenyl-2ethyl- 5-hydroxyphenoxy)propoxy]phenyl]]propanoic acid ethyl ester followed by sodium salt formation and purification as described above in Example 1C provided 601 mg (54%) of the title product as a fluffy white solid:

$^1$H-NMR (DMSO-d$_6$) 7.56 (d, J=7 Hz, 2H), 7.47 (s, 1H), 7..35–7.44 (m, 4H), 7.26 (t, J=7 Hz, 1H), 6.92 (d, J=8 Hz, 1H), 6.71 (s, 1H), 4.26 (t, J=7 Hz, 2H), 4.12 (t, J=6 Hz, 2H), 2.82 (t, J=7 Hz, 2H), 2.49 (m, 5H), 2.20 (m, 4H), 1.08 (t, J=7 Hz, 3H); MS-FAB (m/e) 485 (33), 464 (33), 463 (100), 317 (30); IR (CHCl$_3$, cm$^{-1}$) 3450 (b), 2976, 1632, 1610, 1560, 1373, 1246, 1163, 1060. Anal. (C$_{28}$H$_{28}$O$_6$Na$_2$):

|  | C | H |
|---|---|---|
| Theory | 66.40 | 5.57 |
| Found | 66.11 | 5.81 |

EXAMPLE 12

Preparation of 4-[4-[3-(4-acetyl-2-ethyl-5hydroxyphenoxy)propoxy]benzoic acid sodium salt hydrate

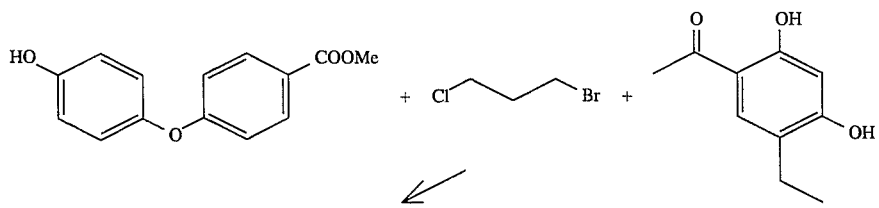

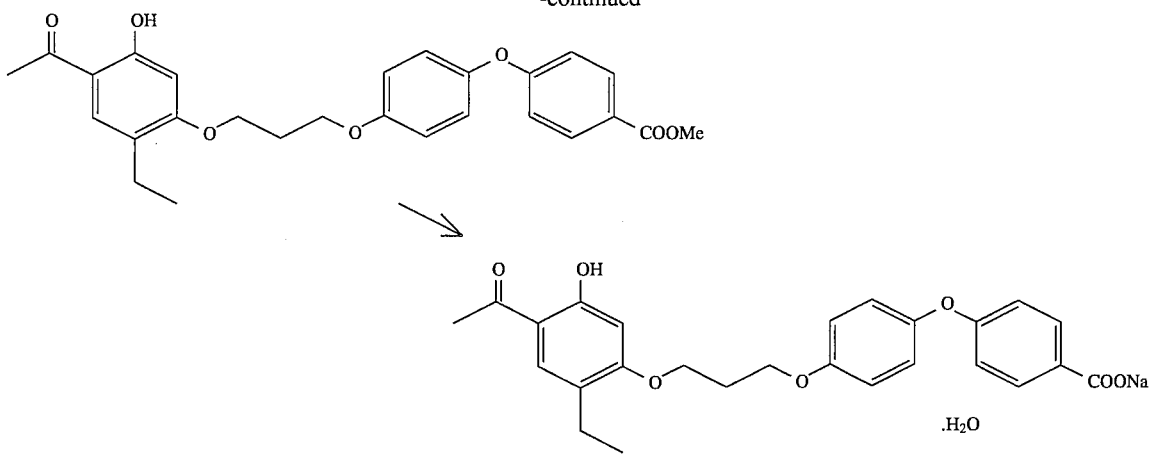

A. 4-[4-[3-(4-Acetyl-2-ethyl-5-hydroxyphenoxy)propoxy]phenoxy]benzoic acid methyl ester.

4-(4-Hydroxyphenoxy)benzoic acid methyl ester (1.00 g, 4.10 mmol) was alkylated with 1-bromo-3-chloropropane followed by 2,4-dihydroxy-5-ethylacetophenone as described above in Example 2A to provide a brown oil. Silica gel chromatography (hexane/ethyl acetate) provided 900 mg (62%) of the title intermediate as a colorless oil:

$^1$H-NMR (CDCl$_3$) 12.73 (s, 1H, —OH), 7.98 (d, J=9 Hz, 2H), 7.45 (s, 1H), 7.05 (d, J=9 Hz, 2H), 6.90 (m, 4H), 6.40 (s, 1H), 4.25 (t, J=6 Hz, 2H), 4.20 (t, J=6 Hz, 2H), 3.89 (s, 3H), 2.65 (m, 5H), 2.35 (quintet, J=6 Hz, 2H), 1.20 (t, J=7 Hz, 3H).

B. 4-[4-[3-(4-Acetyl-2-ethyl-5-hydroxyphenoxy)propoxy]phenoxy]benzoic acid sodium salt hydrate.

Hydrolysis of 900 mg of 4-[4-[3-(4-acetyl-2-ethyl-5-hydroxyphenoxy)propoxy]phenoxy]benzoic acid methyl ester followed by sodium salt formation and purification as described above in Example 1C provided 330 mg (36%) of the title product as a fluffy white solid:

$^1$H-NMR (DMSO-d$_6$) 7.84 (d, J=9 Hz, 2H), 7.60 (s, 1H), 6.95 (s, 4H), 6.78 (d, J=9 Hz, 2H), 6.52 (s, 1H), 4.17 (t, J=6 Hz, 2H), 4.12 (t, J=6 Hz, 2H), 2.50 (m, 5H), 2.16 (quintet, J=6 Hz, 2H), 1.08 (t, J=7 Hz, 3H); MS-FAB (m/e) 473 (p+1, 13), 451 (48), 450 (32), 433 (100); IR (KBr, cm$^{-1}$) 3426 (b), 2964, 1636, 1601, 1501, 1410, 1231, 1162, 1071. Anal. (C$_{26}$H$_{25}$O$_7$Na . H$_2$O):

|  | C | H |
|---|---|---|
| Theory | 63.61 | 5.50 |
| Found | 63.79 | 5.38 |

EXAMPLE 13

Preparation of 2-[3-[3-(4-acetyl-2-ethyl-5-hydroxyphenoxy)propoxy]phenoxy]benzoic acid disodium salt hemihydrate

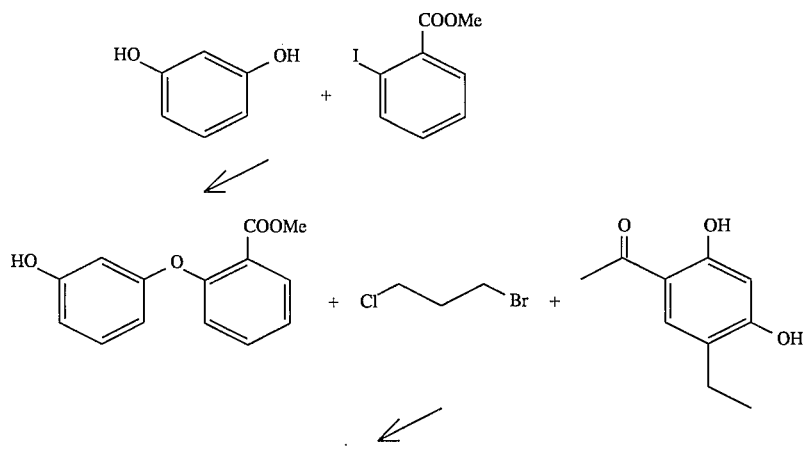

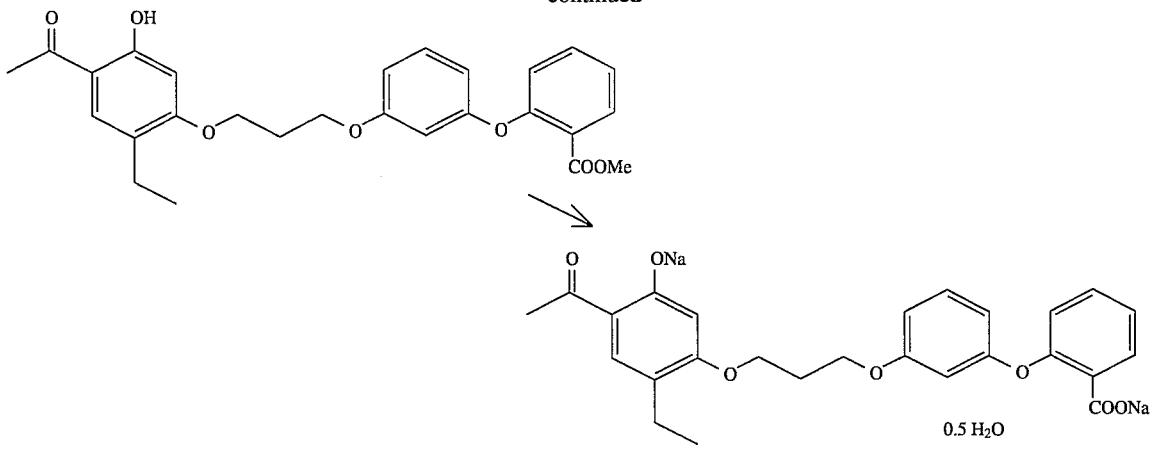

A. 2-(3-Hydroxyphenoxy) benzoic acid methyl ester.

A mixture of resorcinol (8.40 g, 76.3 mmol), methyl 2-iodobenzoate (20.0 g, 76.3 mmol), copper bronze (5.82 g, 91.6 mmol), and potassium carbonate (10.5 g, 76.3 mmol) in pyridine (250 mL) was refluxed for 18 hours. The mixture was cooled to room temperature and filtered. The resulting dark solution was concentrated in vacuo. The resulting oil was dissolved in methylene chloride and washed twice with aqueous 2N hydrochloric acid solution. The organic layer was separated and diluted with hexane resulting in a precipitate. The mixture was filtered and the filtrate allowed to stand for 24 hours. The resulting brown crystals were collected via vacuum filtration and washed with hexane. Silica gel chromatography of this material provided 5.47 g (29%) of the title intermediate as a white crystalline solid:

mp 96° C.; $^1$H-NMR (DMSO-$d_6$) 9.56 (s, 1H), 7.80 (d, J=8 Hz, 1H), 7.57 (t, J=8 Hz, 1H), 7.25 (t, J=8 Hz, 1H), 7.11 (t, J=8 Hz, 1H), 7.03 (d, J=8 Hz, 1H), 6.49 (d, J=8 Hz, 1H), 6.34 (d, J=8 Hz, 1H), 6.27 (s, 1H), 3.70 (s, 3H); MS-EI (m/e) 245 (p+1, 15), 244 (78), 213 (100); IR (KBr, cm$^{-1}$) 3376 (b), 1711, 1600, 1480, 1260, 1124, 1089. Anal. ($C_{14}H_{12}O_4$):

|  | C | H |
|---|---|---|
| Theory | 68.85 | 4.95 |
| Found | 68.66 | 4.99 |

B. 2-[3-[3-(4-Acetyl-2-ethyl-5-hydroxyphenoxy)propoxy]phenoxy]benzoic acid methyl ester.

2-(3-Hydroxyphenoxy)benzoic acid methyl ester (1.25 g, 5.12 mmol) was alkylated with 1-bromo-3-chloropropane 20 followed by 2,4-dihydroxy-5-ethylacetophenone as described above in Example 2A to provide the title intermediate as a white solid:

$^1$H-NMR (CDCl$_3$) 12.73 (s, 1H, —OH), 7.90 (d, J=9 Hz, 1H), 7.47 (t, J=8Hz, 1H), 7.39 (s, 1H), 7.25 (m, 2H), 7.05 (d, J=9 Hz, 1H), 6.68 (d, J=8 Hz, 1H), 6.53 (m, 2H), 6.36 (s, 1H), 4.25 (t, J=6 Hz, 2H), 4.15 (t, J=6 Hz, 2H), 3.80 (s, 3H), 2.22 (m, 5H), 2.30 (quintet, J=6 Hz, 2H), 1.27 (t, J=7 Hz, 3H).

C. 2-[3-[3-(4-Acetyl-2-ethyl-5-hydroxyphenoxy)propoxy]phenoxy]benzoic acid disodium salt hemihydrate.

Hydrolysis of 1.05 g of 2-[3-[3-(4-acetyl-2-ethyl-5-hydroxyphenoxy)propoxy]phenoxy]benzoic acid methyl ester followed by sodium salt formation and purification as described above in Example 1C provided 140 mg (13%) of the title product as a fluffy white solid:

$^1$H-NMR (DMSO-$d_6$) 7.55 s, 1H), 7.43 (d, J=9 Hz, 1H), 7.00–7.20 (m, 3H), 6.77 (d, J=9 Hz, 1H), 6.50 (d, J=8 Hz, 1H), 6.47 (s, 1H), 6.35 (m, 2H), 4.07 (m, 4H), 2.50 (s, 3H), 2.47 (m, 2H), 2.12 (quintet, J=6 Hz, 2H), 1.07 (t, J=7 Hz, 3H); MS-FAB (m/e) 495 (p+1, 89), 473 (100). Anal. ($C_{26}H_{24}O_7Na_2 \cdot 0.5H_2O$):

|  | C | H |
|---|---|---|
| Theory | 62.03 | 4.96 |
| Found | 62.48 | 5.21 |

EXAMPLE 14

Preparation of 3-[3-[3-(4-acetyl-2-ethyl-5-hydroxyphenoxy)propoxy]phenoxy]benzoic acid disodium salt hemihydrate.

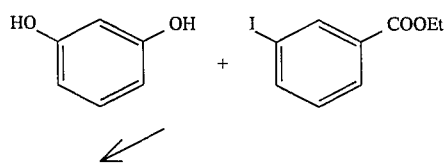

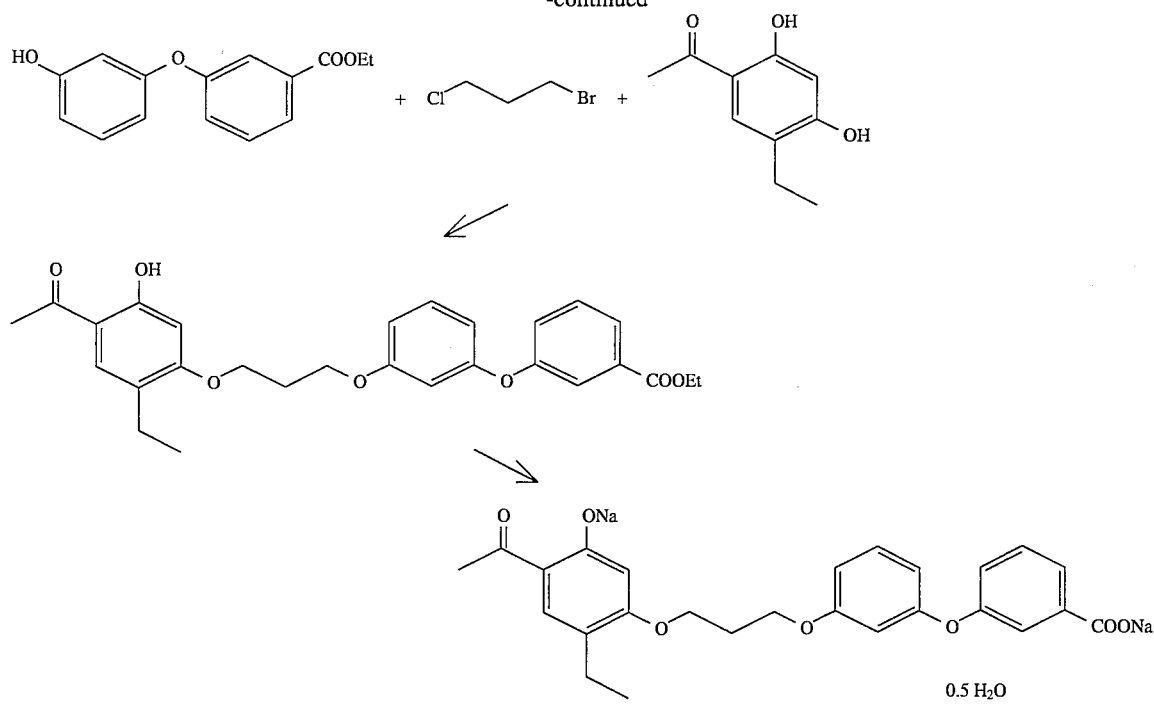

A. 3-(3-Hydroxyphenoxy)benzoic acid ethyl ester.

Ethyl 3-iodobenzoate (21.1 g, 76.3 mmol) was coupled to resorcinol as described above in Example 7A. The dark oil from the initial concentration was dissolved in methylene chloride and filtered through Florisil™. The filtrate was concentrated in vacuo and the resulting oil dissolved in ethyl acetate. This solution was washed thrice with saturated copper sulfate solution. The organic layer was dried (sodium sulfate), filtered, and concentrated in vacuo to provide a clear dark oil. Silica gel chromatography (hexane/ethyl acetate) provided 4.51 g (23%) of the title intermediate as a colorless oil:

$^1$H-NMR (CDCl$_3$) 7.81 (d, J=9 Hz, 1H), 7.71 (s, 1H), 7.42 (t, J=8 Hz, 1H), 7.18–7.25 (m, 2H), 6.59 (m, 2H), 6.50 (s, 1H), 5.39 (s, 1H, —OH), 4.38 (q, J=7 Hz, 2H), 1.28 (t, J=7 Hz, 3H); MS-FD (m/e) 259 (p+1, 29), 258 (100); IR (CHCl$_3$, cm$^{-1}$) 3300 (b), 1717, 1599, 1587, 1483, 1283, 1138. Anal (C$_{15}$H$_{14}$O$_4$):

|  | C | H |
|---|---|---|
| Theory | 69.76 | 5.46 |
| Found | 69.49 | 5.35 |

B. 3-[3-[3-(4-Acetyl-2-ethyl-5-hydroxyphenoxy)propoxy]phenoxy]benzoic acid ethyl ester.

3-(3-Hydroxyphenoxy)benzoic acid ethyl ester (670 mg, 2.60 mmol) was alkylated with 1-bromo-3-chloropropane followed by 2,4-dihydroxy-5-ethylacetophenone as described above in Example 2A to provide 860 mg (69%) of the title intermediate as a golden oil:

$^1$H-NMR (CDCl$_3$) 12.73 (s, 1H, —OH), 7.80 (d, J=9 Hz, 1H), 7.70 (s, 1H), 7.38 (m, 2H), 7.20 (m, 2H), 6.68 (d, J=8 Hz, 1H), 6.65 (m, 2H), 6.38 (s, 1H), 4.35 (q, J=7 Hz, 2H), 4.20 (m, 4H), 2.60 (m, 5H), 2.30 (quintet, J=6 Hz, 2H), 1.28 (t, J=7 Hz, 3H), 1.20 (t, J=7 Hz, 3H).

C. 3-[3-[3-(4-Acetyl-2-ethyl-5-hydroxyphenoxy)propoxy]phenoxy]benzoic acid disodium salt hemihydrate.

Hydrolysis of 860 mg of 3-[3-[3-(4-acetyl-2-ethyl-5-hydroxyphenoxy)propoxy]phenoxy]benzoic acid ethyl ester followed by sodium salt formation and purification as described above in Example 1C provided 100 mg (11%) of the title product as a fluffy white solid:

$^1$H-NMR (DMSO-d$_6$) 7.60 (m, 2H), 7.41 (d, J=2 Hz, 1H), 7.25 (m, 2H), 6.84 (d, J=8 Hz, 1H), 6.66 (d, J=8 Hz, 1H), 6.48 (m, 3H), 4.14 (m, 4H), 2.53 (s, 3H), 2.48 (m, 2H), 2.15. (quintet, J=5 Hz, 2H), 1.06 (t, J=7 Hz, 3H); MS-FAB (m/e) 495 (p+1, 97), 473 (100); IR (KBr, cm$^{-1}$) 3400 (b), 2964, 1601, 1564, 1404, 1269, 1223, 1144, 768. Anal. (C$_{26}$H$_{24}$O$_7$Na$_2$ · H$_2$O):

|  | C | H |
|---|---|---|
| Theory | 61.97 | 4.97 |
| Found | 61.78 | 5.03 |

EXAMPLE 15

Preparation of 3-[4-[7-carboxy-3-[3-(4-acetyl-2-ethyl-5-hydroxyphenoxy)propoxy]-9-oxo-9H-xanthene]] propanoic acid trisodium salt trihydrate

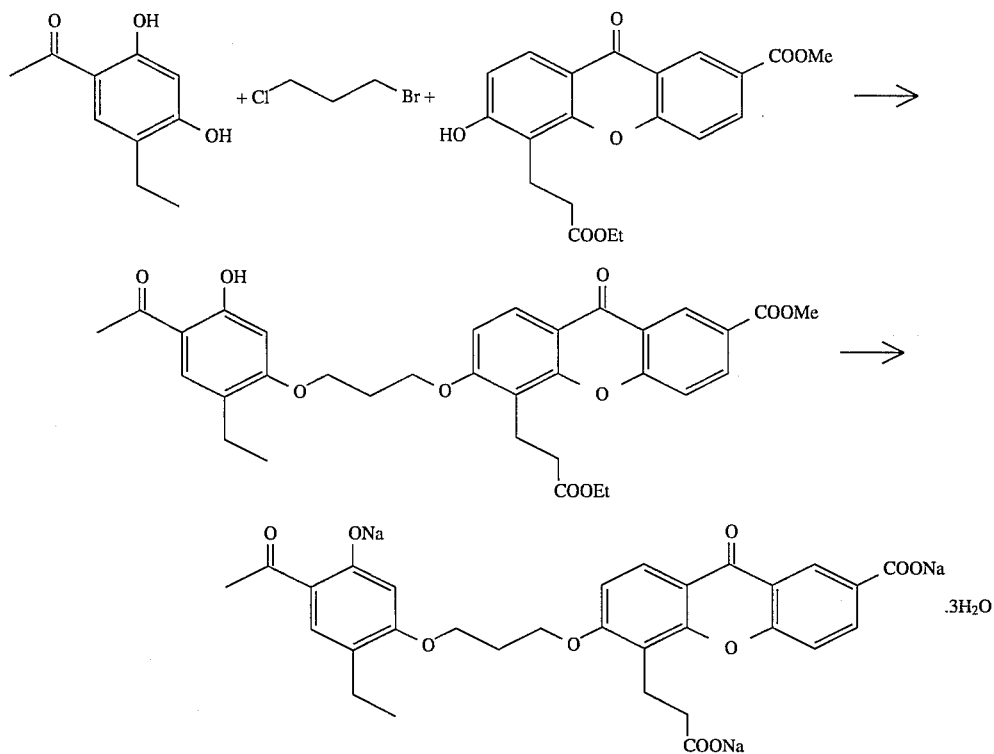

A. 3-[4-[7-Carbomethoxy-3-[3-(4-acetyl-2-ethyl- 5-hydroxyphenoxy)propoxy]-9-oxo-9H-xanthene]]propanoic acid ethyl ester.

A mixture of 3-[4-(7-carbomethoxy-3-hydroxy-9-oxo-9H-xanthene)]propanoic acid ethyl ester (1.20 mg, 3.24 mmol), 1-bromo-3-chloropropane (520 mg, 3.31 mmol), and potassium carbonate (2.30 g, 16.7 mmol) in dimethylformamide (25 mL) was stirred at room temperature for 18 hours. The mixture was diluted with ethyl acetate and washed once with water. The organic layer was dried (sodium sulfate), filtered, and concentrated in vacuo to provide a colorless oil. This material was alkylated with 2,4-dihydroxy-5-ethylacetophenone as described above in Example 2A to provide 1.70 mg (88%) of the title intermediate as a white solid:

$^1$H-NMR (CDCl$_3$) 9.01 (s, 1H), 8.38 (d, J=9 Hz, 1H), 8.27 (d, J=9 Hz, 1H), 7.58 (d, J=9 Hz, 1H), 7.45 (s, 1H), 7.03 (d, J=8 Hz, 1H), 6.43 (s, 1H), 4.36 (t, J=6 Hz, 2H), 4.27 (t, J=6 Hz, 2H), 4.12 (quartet, J=5 Hz, 2H), 3.97 (s, 3H), 3.29 (t, J=6 Hz, 2H), 2.55 (m, 7H), 2.43 (quintet, J=6 Hz, 2H), 1.20 (t, J=7 Hz, 3H), 1.12 (t, J=7 Hz, 3H).

B. 3-[4-[7-Carboxy-3-[3-(4-acetyl-2-ethyl-5-hydroxyphenoxy)propoxy]- 9-oxo-9H-xanthene]]propanoic acid trisodium salt trihydrate.

Hydrolysis of 1.60 g of 3-[4-[7-carbomethoxy-3-[3-(4-acetyl- 2-ethyl-5-hydroxyphenoxy)propoxy]-9-oxo-9H-xanthene]]propanoic acid ethyl ester followed by sodium salt formation and purification as described above in Example 1C provided 900 mg (53%) of the title product as a fluffy white solid:

$^1$H-NMR (DMSO-d$_6$) 8.62 (d, J=2 Hz, 1H), 8.29 (dd, J=8, 2 Hz, 1H), 8.02 (d, J=8 Hz, 1H), 7.52 (d, J=8 Hz, 1H), 7.44 (s, 1H), 7.15 (d, J=9 Hz, 1H), 6.72 (s, 1H), 4.23 (m, 4H), 3.08 (m, 2H), 2.49 (m, 5H), 2.12 (m, 4H), 1.03 (t, J=7 Hz, 3H); 593 (p+1, 100), 571 (95), 549 (23); IR (mull, cm$^{-1}$) 3400 (b), 1610, 1600, 1590, 1462, 1377, 1273. Anal. (C$_{30}$H$_{25}$O$_{10}$Na$_3$ . 3H$_2$O):

|  | C | H |
|---|---|---|
| Theory | 53.89 | 4.64 |
| Found | 53.48 | 4.42 |

EXAMPLE 16

Preparation of [2-[7-[3-(4-acetyl-2-ethyl-5-hydroxypphenoxy)propoxy]naphthalenyl]oxy]acetic acid sodium salt hydrate

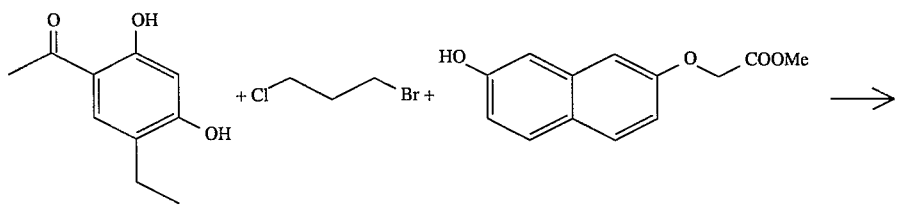

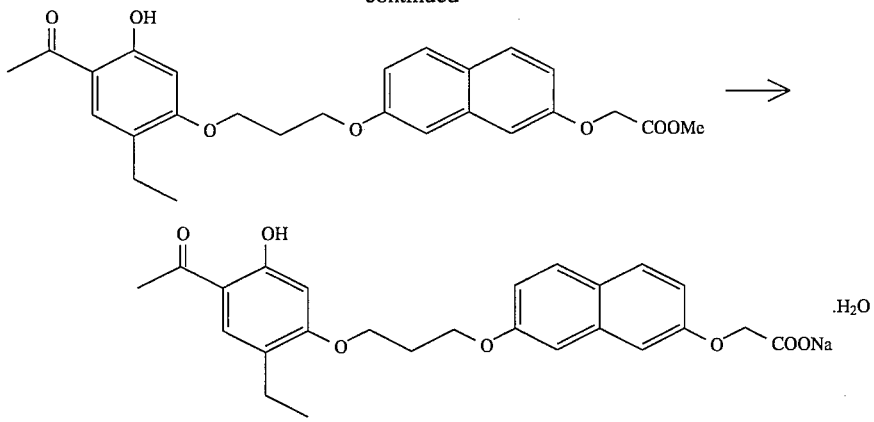

A. [2-[7-[3-(4-Acetyl-2-ethyl-5-hydroxyphenoxy)propoxy]naphthalenyl]oxy]acetic acid methyl ester.

[2-(7-Hydroxynaphthalenyl)oxy]acetic acid methyl ester (J. Med. Chem., 30, 173 (1987); 1.00 g, 4.29 mmol) was alkylated with 1-bromo-3-chloropropane followed by 2,4-dihydroxy-5-ethylacetophenone as described above in Example 9A to provide 460 mg (23%) of the title intermediate as a white solid:

$^1$H-NMR (CDCl$_3$) 7.70 (d, J=9 Hz, 1H), 7.68 (d, J=8 Hz, 1H), 7.43 (s, 1H), 6.95–7.15 (m, 4H), 6.44 (s, 1H), 4.75 (s, 2H), 4.29 (t, J=6 Hz, 2H), 4.22 (t, J=6 Hz, 2H), 3.84 (s, 3H), 2.59 (m, 5H), 2.35 (quintet, J=6 Hz, 2H), 1.20 (t, J=7 Hz, 3H).

B. [2-[7-[3-(4-Acetyl-2-ethyl-5-hydroxyphenoxy)propoxy]naphthalenyl]oxy]acetic acid sodium salt hydrate.

Hydrolysis of 460 mg of [2-[7-[3-(4-acetyl-2-ethyl-5-hydroxyphenoxy)propoxy]naphthalenyl]oxy]acetic acid methyl ester followed by sodium salt formation and purification as described above in Example 1C provided 120 mg (24%) of the title product as a fluffy white solid:

$^1$H-NMR (DMSO-d$_6$) 7.63 (m, 2H), 7.59 (s, 1H), 7.12 (s, 1H), 6.85–7.03 (m, 3H), 6.50 (s, 1H), 4.21 (m, 6H), 2.50 (m, 5H), 2.21 (quintet, J=6 Hz, 2H), 1.08 (t, J=7 Hz, 3H); MS-FAB (m/e) 483 (p+1, 35), 461 (100), 309 (33); IR (KBr, cm$^{-1}$) 3426 (b), 2964, 1632, 1625, 1387, 1256, 1211, 1163, 1055, 834. Anal. (C$_{25}$H$_{24}$O$_7$Na$_2$ · H$_2$O):

|  | C | H |
|---|---|---|
| Theory | 59.95 | 5.20 |
| Found | 60.06 | 5.30 |

EXAMPLE 17

Preparation of 2-[[3-[3-(4-acetyl-2-ethyl-5-hydroxyphenoxy)propoxy]-2-propylphenoxy]methyl]benzoic acid disodium salt hemihydrate

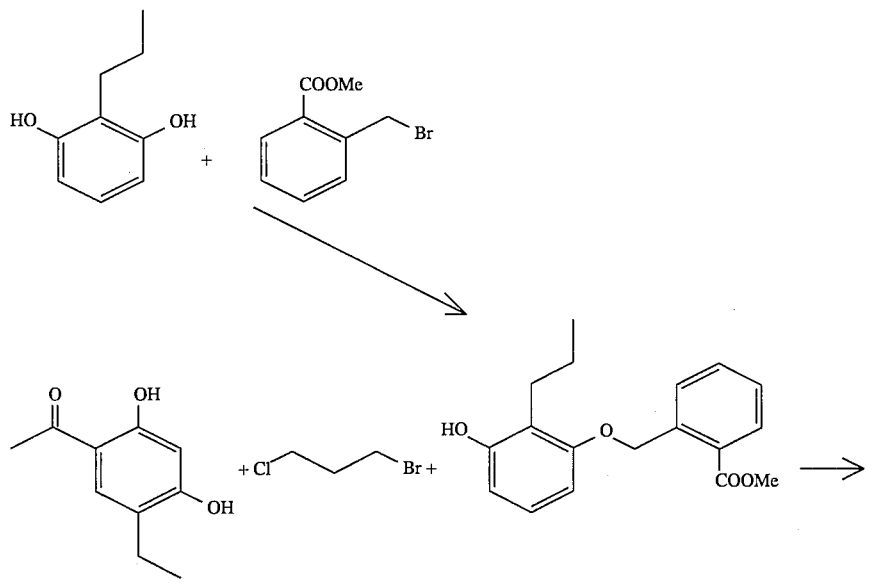

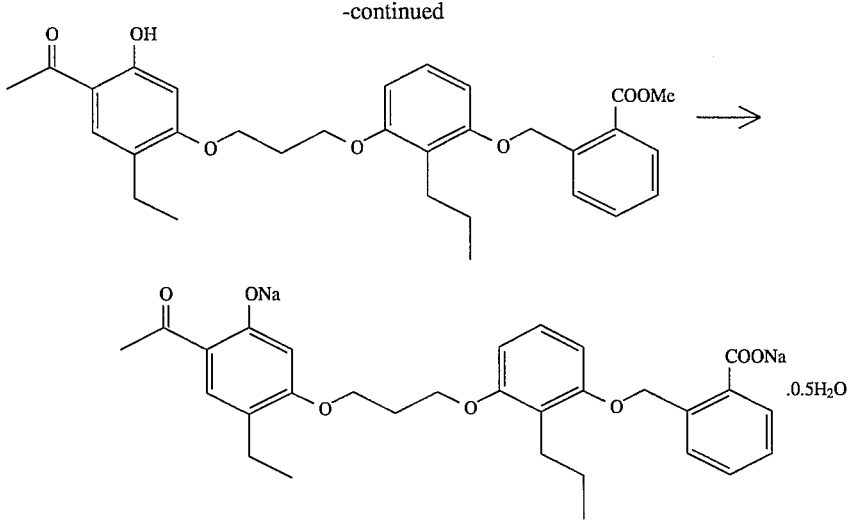

-continued

A. 2-[(3-Hydroxy-2-propylphenoxy)methyl]benzoic acid methyl ester.

A mixture of 1,3-dihydroxy-2-propylbenzene (5.00 g, 33.3 mmol) in dimethylformamide (10 mL) was treated with sodium hydride (880 mg, 36.6 mmol) as room temperature for 20 minutes. 2-(Carbomethoxy)benzyl bromide (7.62 g, 33.3 mmol) was added in one portion and the resulting mixture stirred at room temperature for 24 hours. The mixture was diluted with ethyl acetate and washed once with brine. The organic layer was dried (sodium sulfate), filtered, and concentrated in vacuo to provide a brown oil. Silica gel chromatography (hexane/ethyl acetate) provided 2.10 g (21%) of the title intermediate as a colorless oil:

$^1$H-NMR (CDCl$_3$) 8.08 (d, J=8 Hz, 1H), 7.84 (d, J=8 Hz, 1H), 7.61 (t, J=8 Hz, 1H), 7.41 (t, J=8 Hz, 1H), 7.02 (t, J=8 Hz, 1H), 6.58 (d, J=8 Hz, 1H), 6.50 (d, J=8 Hz, 1H), 5.52 (s, 2H), 5.16 (s, 1H, —OH), 3.94 (s, 3H), 2.78 (t, J=7 Hz, 2H), 1.67 (hextet, J=8 Hz, 2H), 1.03 (t, J=8 Hz, 3H).

B. 2-[[3-[3-(4-Acetyl-2-ethyl-5-hydroxyphenoxy)propoxy]-2propylphenoxy]methyl]benzoic acid disodium salt hemihydrate.

2-[(3-Hydroxy-2-propylphenoxy)methyl]benzoic acid methyl ester (500 mg, 17.5 retool) was alkylated with 1-bromo-3-chloropropane followed by 2,4-dihydroxy-5-ethylacetophenone as described above in Example 9A. Hydrolysis of the crude product followed by sodium salt formation and purification as described above in Example 1C provided 75 mg (8%) of the title product as a fluffy white solid:

$^1$H-NMR (DMSO-d$_6$) 7.66 (d, J=8 Hz, 1H), 7.60 (s, 1H), 7.40 (d, J=8 Hz, 1H), 7.19 (t, J=9 Hz, 1H), 7.13 (t, J=7 Hz, 1H), 7.02 (t, J=8 Hz, 1H), 6.60 (d, J=8 Hz, 1H), 6.53 (d, J=8 Hz, 1H), 6.49 (s, 1H), 5.47 (s, 2H), 4.22 (t, J=6 Hz, 2H), 4.11 (t, J=6 Hz, 2H), 2.63 (t, J=5 Hz, 2H), 2.53 (s, 3H), 2.49 (m, 2H), 2.20 (quintet, J=5 Hz, 2H), 1.45 (hextet, J=8 Hz, 2H), 1.07 (t, J=7 Hz, 3H), 0.83 (t, J=7 Hz, 3H); MS-FAB (m/e) 550 (p+1, 47), 529 (100); IR (KBr, cm$^{-1}$) 3450 (b), 2955, 1688, 1688, 1637, 1593, 1462, 1373, 1271, 1131, 1065. Anal. (C$_{30}$H$_{32}$O$_7$Na$_2$ . 0.5H$_2$O):

|  | C | H |
|---|---|---|
| Theory | 64.40 | 5.94 |
| Found | 64.38 | 6.24 |

EXAMPLE 18

Preparation of 2-[3-[4-(4-acetyl-2-ethyl-5-hydroxyphenoxy) butoxy]-2-propylphenoxy]benzoic acid disodium salt

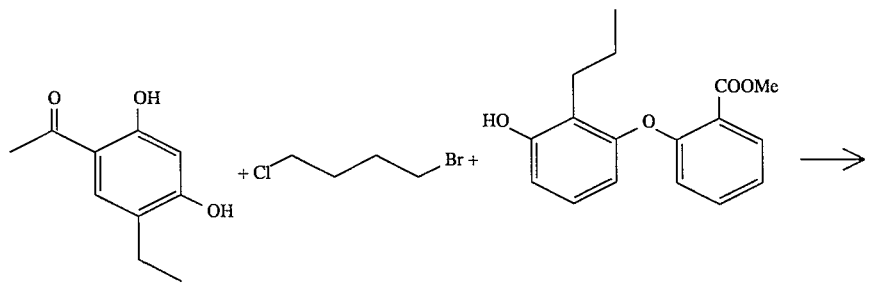

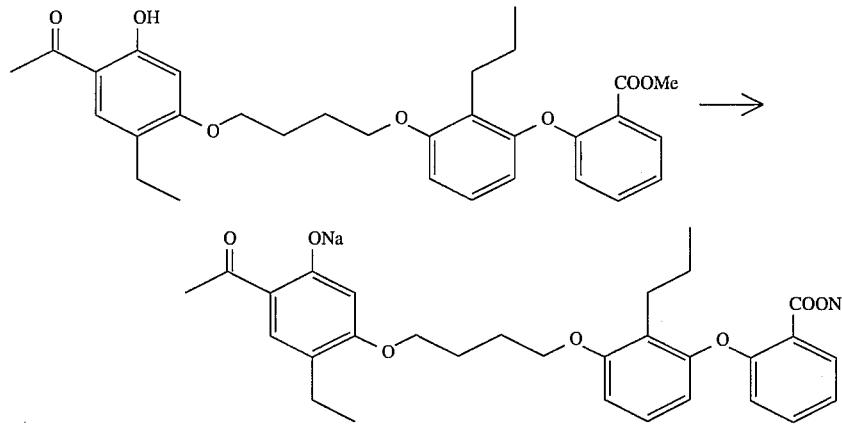

A. 2-[3-[4-(4-Acetyl-2-ethyl-5-hydroxyphenoxy)butoxy]-2-propyl-phenoxy]benzoic acid methyl ester.

2-(3-Hydroxy-2-propylphenoxy)benzoic acid methyl ester (Lilly patent application X-8167; 1.20 g, 4.20 mmol) was alkylated with 1-bromo-4-chlorobutane followed by 2,4-dihydroxy-5-ethylacetophenone as described above in Example 9A to provide 620 mg (28%) of the title intermediate as a colorless oil:

$^1$H-NMR (CDCl$_3$) 7.92 (d, J=9 Hz, 1H), 7.45 (s, 1H), 7.39 (t, J=8 Hz, 1H), 7.10 (m, 2H), 7.86 (d, J=9 Hz, 1H), 7.67 (d, J=8 Hz, 1H), 7.47 (d, J=9 Hz, 1H), 6.42 (s, 1H), 4.11 (m, 4H), 3.85 (s, 3H), 2.70 (t, J=6 Hz, 2H), 2.60 (m, 5H), 2.08 (m, 4H), 1.63 (hextet, J=8 Hz, 2H), 1.23 (t, J=7 Hz, 3H), 0.96 (t, J=7 Hz, 3H).

B. 2-[3-[4-(4-Acetyl-2-ethyl-5-hydroxyphenoxy)butoxy]-2-propyl-phenoxy]benzoic acid disodium salt.

Hydrolysis of 620 mg of 2-[3-[4-(4-acetyl-2-ethyl-5-hydroxyphenoxy)butoxy]- 2-propylphenoxy]benzoic acid methyl ester followed by sodium salt formation and purification as described above in Example 1C provided 262 mg (40%) of the title product as a fluffy white solid:

$^1$H-NMR (DMSO-d$_6$) 7.59 (s, 1H), 7.38 (dd, J=7, 2 Hz, 1H), 7.08 (t, J=8 Hz, 1H), 6.96 (m, 2H), 6.62 (d, J=8 Hz, 1H), 6.57 (d, J=9 Hz, 1H), 6.51 (s, 1H), 6.25 (d, J=8 Hz, 1H), 4.09 (m, 2H), 4.02 (m, 2H), 2.58 (t, J=8 Hz, 2H), 2.53 (s, 3H), 2.48 (m, 2H), 1.90 (m, 4H), 1.47 (hextet, J=7 Hz, 2H), 1.10 (t, J=7 Hz, 3H), 0.82 (t, J=7 Hz, 3H); MS-FAB (m/e) 552 (p+2, 35), 551 (p+1, 97), 529 (100); IR (KBr, cm$^{-1}$) 3470 (b), 2972, 1633, 1604, 1373, 1268, 1112, 1050. Anal. (C$_{30}$H$_{32}$O$_7$Na$_2$):

|  | C | H |
| --- | --- | --- |
| Theory | 65.39 | 5.81 |
| Found | 65.15 | 6.03 |

EXAMPLE 19

Preparation of 2-[3-[3-(4-Acetyl-2-ethyl-5-hydroxyphenoxy)propoxy]-2-propylphenoxy]benzoic acid disodium salt hydrate

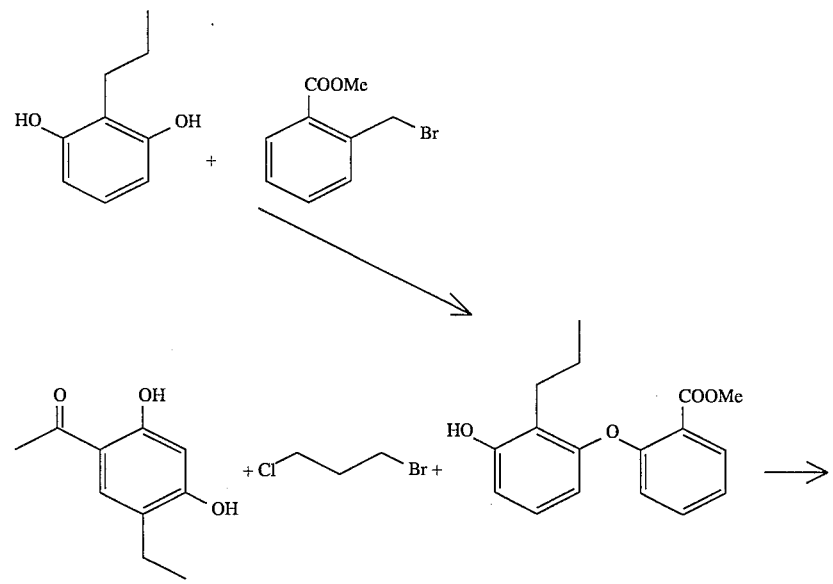

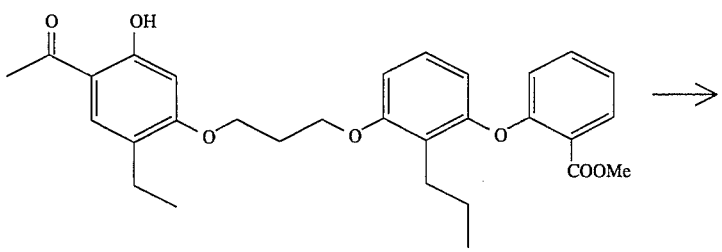

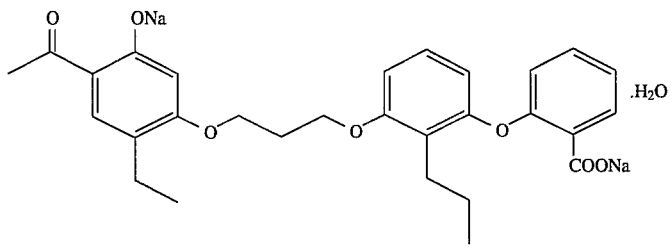

2-(3-Hydroxy-2-propylphenoxy)benzoic acid metal ester (1.10 g, 3.85 mmol) was alkylated with 1-bromo-3-chloropropane followed by 2,4-dihydroxy-5-ethylacetophenone as described above in Example 9A. Hydrolysis of the crude product followed by sodium salt formation and purification as described above in Example 1C provided 510 mg (35%) of the title product as a fluffy white solid:

$^1$H-NMR (DMSO-$d_6$) 7.57 (s, 1H), 7.41 (dd, J=7, 2 Hz, 1H), 7.08 (t, J=8 Hz, 1H), 6.96 (m, 2H), 6.64 (d, J=8 Hz, 1H), 6.57 (d, J=8 Hz, 1H), 6.52 (s, 1H), 6.26 (d, J=8 Hz, 1H), 4.19 (t, J=6 Hz, 2H), 4.12 (t, J=6 Hz, 2H), 2.58 (t, J=7 Hz, 2H), 2.52 (s, 3H), 2.50 (m, 2H), 2.19 (quintet, J=6 Hz, 2H), 1.42 (hextet, J=7 Hz, 2H), 1.07 (t, J=8 Hz, 3H), 0.79 (t, J=7 Hz, 3H); MS-FAB (m/e) 538 (p+2, 28), 537 (p+1, 82), 545 (100); IR (KBr, cm$^{-1}$) 3415 (b), 2962, 1632, 1600, 1460, 1391, 1268, 1115. Anal ($C_{29}H_{30}O_7Na_2 \cdot H_2O$):

|  | C | H |
|---|---|---|
| Theory | 62.81 | 5.82 |
| Found | 62.71 | 6.09 |

EXAMPLE 20

Preparation of
3-[1-[2-[3-(4-acetyl-2-ethyl-5-hydroxyphenoxy)propoxy]-5-(3-carboxybenzoyl)phenyl]]propanoic acid trisodium salt hydrate

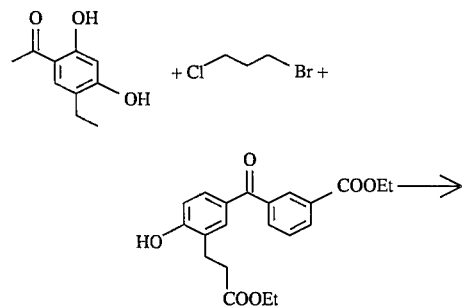

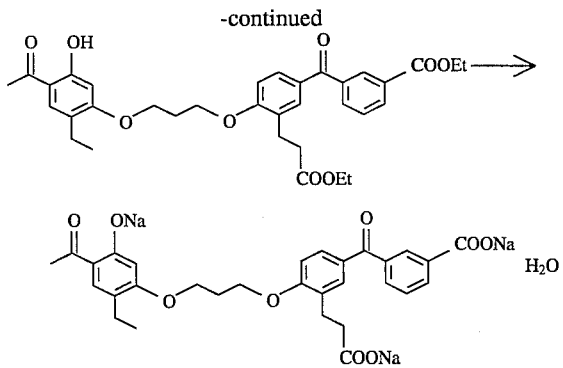

3-[1-[2-Hydroxy-5-(3-carboethoxybenzoyl)phenyl]]propanoic acid ethyl ester (Gapinski, D. M.; Mallet, B. E.; Froelich, L. L.; Jackson, W. T., J. Med. Chem., 33, 2798–2813 (1990); 450 mg, 1.22 mmol) was alkylated with 1-bromo-3-chloropropane followed by 2,4-dihydroxy-5-ethylacetophenone as described above Example 9A. Hydrolysis of the crude product followed by sodium salt formation and purification as described above in Example 1C provided 260 mg (35%) of the title product as a fluffy white solid:

$^1$H-NMR (DMSO-$d_6$) 8.16 (s, 1H), 8.09 (d, J=8 Hz, 1H), 7.64 (d, J=8 Hz, 1H), 7.55 (m, 2H), 7.43 (m, 2H), 7.07 (d, J=8 Hz, 1H), 6.67 (s, 1H), 4.22 (m, 4H), 2.78 (t, J=7 Hz, 2H), 2.49 (s, 3H), 2.43 (m, 2H), 2.19 (m, 4H), 1.07 (t, J=7 Hz, 3H); MS-FAB (m/e) 602 (p+2, 9), 601 (p+1, 36), 580 (45), 579 (100), 557 (91); IR (KBr, cm$^{-1}$) 3433 (b), 1650, 1602, 1590, 1392, 1267. Anal. ($C_{30}H_{27}O_9Na_3 \cdot H_2O$):

|  | C | H |
|---|---|---|
| Theory | 58.26 | 4.73 |
| Found | 58.57 | 4.57 |

LTB$_4$ ANTAGONISM

The compounds of our Formulas should be useful in treating any condition, including clinical conditions, which is characterized by the excessive release of leukotriene B$_4$.

These conditions include immediate type hypersensitivity reactions such as asthma. The term "excessive release" of leukotriene $B_4$ refers to an amount of the leukotriene sufficient to cause the particular condition associated with such amount. The amount of leukotriene which is considered to be excessive will depend on a variety of factors, including the amount of leukotriene required to cause the particular condition, and the species of the mammal involved. As will be appreciated by those skilled in the art, the success of treating a mammal suffering from or susceptible to a condition characterized by an excessive release of leukotriene with a compound of our Formulas will be measured by the regression or prevention of the symptoms of the condition. The effectiveness of compounds of our Formulas to inhibit the binding of tritiated $LTB_4$ to guinea pig lung membranes was determined as follows.

$^3$H]-$LTB_4$ Radioligand Binding Assay in Guinea Pig Lung Membranes

[$^3$H]-$LTB_4$ (196–200 Ci/mmole) was purchased from New England Nuclear (Boston, Mass.). All other materials were purchased from Sigma (St. Louis, Mo.). Incubations (555 mL) were performed in polypropylene minitubes for 45 minutes at 30° C. and contained 25 mg of guinea pig lung membrane protein (Saussy, et al., *Mol. Pharmacol.*, 39, 72 (1991)) in a buffer containing 25 mM MOPS, 10 mM $MgCl_2$, 10 mM $CaCl_2$, pH 6.5, approximately 140 pM [$^3$H]-$LTB_4$, and displacing ligand or vehicle (0.1% DMSO in 1 mM sodium carbonate, final concentration) as appropriate. The binding reaction was terminated by the addition of 1 mL ice cold wash buffer (25 mM Tris-HCl, pH 7.5) followed immediately by vacuum filtration over Whatman GF/C glass fiber filters using a Brandel (Gaithersburg, Md.) 48 place harvester. The filters were washed three times with 1 mL of wash buffer. Retained radioactivity was determined by liquid scintillation counting at 50% counting efficiency using Ready Protein Plus cocktail (Beckman, Fullerton, Calif.). Nondisplaceable binding was determined in the presence of 1 mM $LTB_4$ and was usually less than 10% of total binding. Data were analyzed using linear regression analysis-of-log-logit plots of-the values between 10% and 90% of control binding to calculate $IC_{50}$s and slope factors (pseudo-Hill coefficients). $IC_{50}$ values thus obtained were corrected for radioligand concentration (Cheng and Prusoff, *Biochem. Pharmacol.*, 22, 3099 (1973)) to calculate $K_i$ values. The data reported below is the mean —log $K_i$, otherwise known as the pKi, for n experiments.

Inhibition of Binding of $^3$H-$LTB_4$ to Peripheral Human Neutrophils

The effectiveness of compounds to inhibit the binding of leukotriene $B_4$ to a specific receptor on the membrane of human neutrophils was measured by using an adaptation of a radio-ligand binding assay developed by Goldman and Goetzl, *J. Immunol.*, 129, 1600 (1982). Other investigators have developed similar assays (see, e.g., Kreisle, et al., *J. Exp. Med.*, 157, 628 (1983) and Lin, et al., *Prostaglandins*, 28, 837 (1984)).

Cells used in the assay were isolated by standard techniques of centrifugation on Ficoll-Hypaque, dextran 70 sedimentation and hypotonic lysis. The following procedure was used. Freshly-prepared buffy coat layers from two individuals were obtained from a local blood donor center. The cells were mixed and diluted to 484 ml with phosphate buffered saline containing heparin (10 units/ml) and heat-inactivated calf serum (5%). This was divided into 20 ml aliquots and the aliquots layered on top of Ficoll-Paque (12 ml). The material was then centrifuged at 500 g for 40 minutes at room temperature. The resulting upper layer of platelets and mononuclear cells was discarded. The lower layer containing erythrocytes and neutrophils was retained. Buffer was added (1 ml per 4 ml of lower layer) and the suspension mixed. For each milliliter of this mixture, 0.33 ml of 6% Macrodex was added. After stirring the cells were allowed to sediment for 1 hour at 37° C. The resulting erythrocyte pellet was discarded and the neutrophil enriched supernatant fluid centrifuged at 500 g for 10 minutes at 4° C. Erythrocytes still present in this cell pellet were lysed by incubating the cells with 5–8 ml ice-cold distilled water for 30–45 seconds. Subsequently, the volume was made up to 50 ml by addition of ice-cold buffer and the cells resuspended. The suspension was then centrifuged at 300 g for 10 minutes at 4° C. The cells were finally resuspended at a cell density of $2 \times 10^7$ cells/ml in the assay buffer. This buffer consisted of Hanks' balanced salt solution and 0.1% ovalbumin (pH 7.3). This isolation procedure resulted in cell preparations of $\geq$90% neutrophils and $\geq$90% viability.

The radio-ligand binding assay was conducted by incubating neutrophils ($1 \times 10^7$ cells) with 0.1–0.2 nM $^3$H-$LTB_4$ (sp. act. 150–220 Curies/mmol) and test compound ($1 \times 10^{-5}$M and $1 \times 10^{-6}$M) for 10 minutes at 4° C. The amount of bound $^3$H-$LTB_4$ was then measured and compared with the amount bound in the absence of test compound. The assay was carried out in microcentrifuge tubes by adding first 10 µl test compound dissolved in DMSO, followed by adding 20 µl $^3$H-$LTB_4$ diluted in assay buffer, and finally adding 500 µl of the cell suspension. At the end of the 10 minutes incubation, 300 µl of a mixture of dibutyl and dinonyl phthalate (7:2) were added and the tubes centrifuged for 2 minutes in a microcentrifuge. The radioactivity bound to the cell pellet was measured by scintillation spectroscopy. Appropriate corrections for nonspecific bonding of $^3$H-$LTB_4$ were made.

These results are presented in Tables I.

TABLE I

| | BIOLOGICAL ACTIVITY ACETOPHENONES | |
|---|---|---|
| Example No. | Inhibition of [$^3$H]$LTB_4$ Binding to Human Neutrophils $IC_{50}$ (nM) | Inhibition of [$^3$H]$LTB_4$ Binding to Guinea Pig Lung Membranes pKi (nM) |
| 1 | 39.6 | 8.09 ± 0.11 |
| 2 | 39.6 | 8.09 ± 0.11 |
| 3 | 67 | 8.32 ± 0.07 |
| 4 | 23 | 7.82 ± 0.12 |
| 5 | 36 | 7.86 ± 0.25 |
| 6 | 327 | 7.59 ± 0.06 |
| 7 | 190 | 6.13 ± 0.02 |
| 8 | 43 | 8.69 ± 0.06 |
| 9 | 158 | 6.59 (n = 1) |
| 10 | 326 | 6.00 (n = 1) |
| 11 | 115 | 7.55 ± 0.10 |
| 12 | 193 | 6.88 (n = 1) |
| 13 | 291 | 6.74 (n = 1) |
| 14 | 456 | 6.76 (n = 1) |
| 15 | 4 | 9.01 ± 0.09 |
| 16 | 409 | 6.93 ± 0.23 |
| 17 | 127 | 6.77 (n = 1) |
| 18 | 94 | 7.27 ± 0.11 |
| 19 | 24 | 7.46 ± 0.15 |
| 20 | 46 | 8.18 ± 0.08 |

The compounds or formulations of the present invention may be administered to mammals, including humans, by the oral or rectal routes, topically, parenterally, e.g., by injection and by continuous or discontinuous intra-arterial infusion. The formulations may be in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions or emulsions and suspensions in physiologically acceptable media, and sterile packaged powders adsorbed onto a support material for making injectable solutions. Advantageously for this purpose, compositions may be provided in dosage unit form, preferably each dosage unit containing from about 0.5 to about 500 mg (from about 5 to 50 mg in the case of parenteral or inhalation administration, and from about 25 to 500 mg in the case of oral or rectal administration) of any compound of the above Formulas. Dosages from about 0.5 to about 300 mg/kg per day, preferably 0.5 to 200 mg/kg, of active ingredient may be administered, although it will, of course, readily be understood that the amount of the compound or compounds of the above Formulas actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound from the Formulas above mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material which serves as a vehicle, excipient or medium for the active therapeutic substance. Some examples of the diluents or carrier can include pharmaceutically acceptable fillers, inerts, solvents and the like. The carriers, fillers, inerts, and/or diluents may be employed in the pharmaceutical compositions of the present invention and are, for example, lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, and for oral ingestion.

While all of the compounds illustrated above exemplify $LTB_4$ inhibition activity in vitro, we have also discovered that compounds bearing a single acidic group (R5) are considerably more orally bioactive when administered to mammals compared with those compounds bearing two such acidic groups. Thus, a preferred embodiment when administering compounds of our Formulas orally to mammals comprises administering compounds bearing a single acidic $R_5$ functionality, wherein the acidic group is a carboxy group (and/or pharmaceutically acceptable salts thereof).

The following formulation examples may employ as active compounds any of the compounds of this invention. The examples are illustrative only and are not intended to limit the scope of the invention in any way.

Formulation Example 1

Hard gelatin capsules are prepared using the following ingredients:

| | Quantity (mg/capsule) |
|---|---|
| 6-[3-(4-acetyl-2-ethyl-5-hydroxyphenoxy)propoxy]-9-oxo-9H-xanthene-2-carboxylic acid disodium salt sesquihydrate | 250 |
| Starch | 200 |
| Magnesium stearate | 10 |

The above ingredients are mixed and filled into hard gelatin capsules in 460 mg quantities.

Formulation Example 2

A tablet is prepared using the ingredients below:

| | Quantity (mg/tablet) |
|---|---|
| 3-[3-propyl-4-[3-(4-acetyl-2-ethyl-5-hydroxyphenoxy)propoxy]phenoxy]benzoic acid disodium salt | 250 |
| Cellulose, microcrystalline | 400 |
| Silicon dioxide, fumed | 10 |
| Magnesium stearate | 5 |

The components are blended and compressed to form tablets each weighing 665 mg.

Formulation Example 3

An aerosol solution is prepared containing the following components:

| | Weight % |
|---|---|
| 4-[3-propyl-4-[3-(4-acetyl-2-ethyl-5-hydroxyphenoxy)propoxy]phenoxy]-benzoic acid sodium salt hydrate | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to −30° C. and transferred to a filling device. The required amount is then fed to a container and further filled with the pre-mixed propellants 12 and 114 by means of the cold-filled method or pressure-filled method. The valve units are then fitted to the container.

Formulation Example 4

Tablets each containing 60 mg of active ingredient are made up as follows:

| | |
|---|---|
| 2-[2-Propyl-3-[3-[2-ethyl-5-hydroxy-4-(4-fluorophenyl)phenoxy]propoxy]phenoxy]-benzoic acid sodium salt | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation Example 5

Capsules each containing 80 mg of medicament are made as follows:

| | |
|---|---|
| 3-[1-[5-phenyl-2-[3-(4-acetyl-2-ethyl-5-hydroxyphenoxy)propoxy]phenyl]] propanoic acid disodium salt | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation Example 6

Suppositories each containing 225 mg of active ingredient are made as follows:

| | |
|---|---|
| 4-[4-[3-(4-acetyl-2-ethyl-5-hydroxyphenoxy)propoxy]phenoxy]benzoic acid sodium salt hydrate | 225 mg |
| Unsaturated or saturated fatty acid glycerides to | 2,000 mg |

The active ingredient is passed through a No. 60 mesh U.S. sieve and suspended in the fatty acid glycerides previously melted using the minimum heat necessary. The mixture is then poured into a suppository mold of nominal 2 g capacity and allowed to cool.

Formulation Example 7

Suspensions each containing 50 mg of medicament per 5 mL dose are made as follows:

| | |
|---|---|
| 2-[3-[3-(4-acetyl-2-ethyl-5-hydroxyphenoxy)propoxy]phenoxy]benzoic acid disodium salt hemihydrate | 50 mg |
| Sodium carboxymethyl cellulose | 50 mg |
| Sugar | 1 g |
| Methyl paraben | 0.05 mg |
| Propyl paraben | 0.03 mg |
| Flavor | q.v. |
| Color | q.v. |
| Purified water to | 5 mL |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

In summary, we have described the compounds of the Formulas above and their pharmaceutically acceptable salts and demonstrated that these various compounds, and their pharmaceutical formulations are effective in treating leukotriene $B_4$ mediated disease states. These compounds, and their pharmaceutically acceptable salts, and mixtures thereof, are therefore expected to be useful in treating disease states including, but not limited to, inflammation, allergies, arthritis, asthma, endotoxic and septic shock, adult respiratory distress syndrome and any other disease characterized by an excessive release of leukotriene B4.

We claim:

1. A compound represented by the formula:

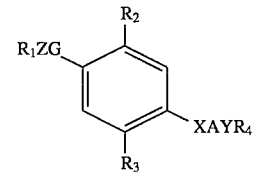

and salts thereof, wherein:

$R_1$ is hydrogen;

$R_2$ is halo, or —OR″;

$R_3$ is $C_1$-$C_{10}$ alkyl, $C_1$-$C_6$ alkanoyl, $C_2$-$C_6$ alkenyl, $C_2$-$C_6$ alkynyl, $C_1$-$C_4$ alkoxy, hydroxy substituted $C_1$-$C_3$ alkyl, or $C_1$-$C_4$ thioalkyl;

X and Y are the same or different and are selected individually at each occurrence from: —CR′$_2$—, —O—, —S—, or —NR′—;

Z is —(CH$_2$)$_n$—, —NR′″— or phenylene;

A is a bond or a linear or branched chain $C_1$-$C_{10}$ alkylidene;

G is —CH$_2$—,

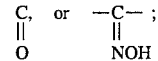

and
wherein:

R′ is independently selected, at each occurrence, from H and $C_{1-4}$ alkyl;

R″ is independently selected, at each occurrence, from H and —(CH$_2$)$_n$—H;

R''' is independently selected, at each occurrence, from H or $C_1$-$C_4$ alkyl;

n is selected independently, at each occurrence, and ranges from 1–8;

m is selected independently, at each occurrence, and ranges from 0–4; and wherein $R_4$ is selected from the groups;

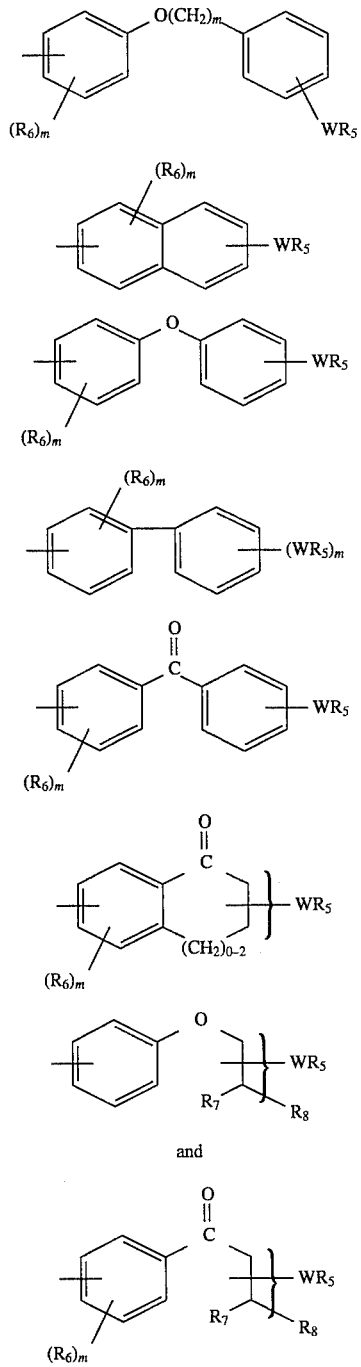

wherein

W is a bond, $-(CHR'\!\!-\!\!)_{\overline{n}}$, $-(O[CHR']_n\!\!-\!\!)_{\overline{n}}$, $-O-$, $-S-$, or

and $R_5$ is H, $C_1$-$C_6$, linear or branched alkyl, $C_2$-$C_6$ alkenyl, $C_2$-$C_6$ alkynyl, hydroxy, 1, 2, 4- triozol-1-yl, cyano, halo, $-N_3$, $-NR'R'''$, $-CO_2R'$, or 5-tetrazolyl optionally substituted with a $C_1$-$C_4$ alkyl group; and $R_6$ is individually selected, at each occurrence, from H, $C_1$-$C_6$ alkyl, $C_2$-$C_6$ alkenyl, $C_2$-$C_6$ alkynyl, phenyl, benzyl, $-WR_5$, halo, thio ($C_1$-$C_4$ alkyl), hydroxy, or $-O-(C_1$-$C_{10}$ alkoxy); and $R_7$ and $R_8$ are both individually selected from H or $C_1$-$C_3$ alkyl; and halo is $-F$, $-Cl$, $-Br$, or $-I$; and pharmaceutically acceptable salts thereof.

2. The compounds of claim 1, or their pharmaceutically acceptable salts, wherein:

X and Y are the same or different and are selected individually, at each occurrence, from $-CH_2-$ or $-O-$;

A is a linear or branched $C_2$-$C_6$ alkylidene;

G is

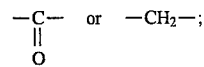

and, $R_4$ is selected from:

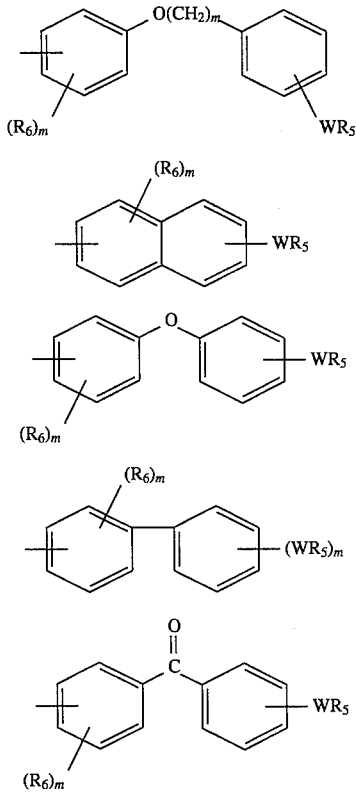

-continued

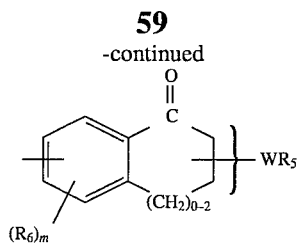

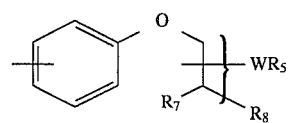

and

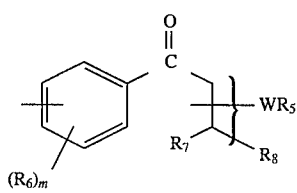

wherein

R$_5$ is —CO$_2$H$_3$ and m ranges from 0–2 and n ranges from 1–6.

3. The compounds of claim 1 and their pharmaceutically acceptable salts, wherein:

X and Y are the same or different and are individually selected, at each occurrence, from: —CH$_2$—, and —O—;

A is a linear or branched C$_2$-C$_6$ alkylidene;

G is

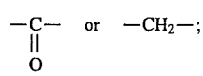

and

R$_2$ is —OH;

W is a bond,

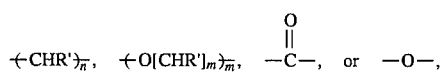

R$_5$ is: —CO$_2$R' or 5-tetrazolyl; and

R$_6$ is independently selected, at each occurrence, from —WR$_5$, —H, C$_1$-C$_4$ alkyl, halo, hydroxy, methoxy, benzyl, or phenyl; and R4 is:

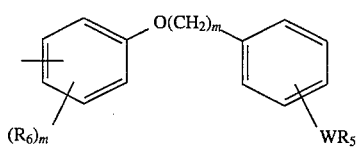

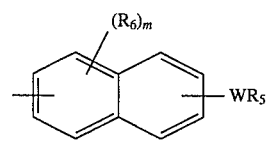

-continued

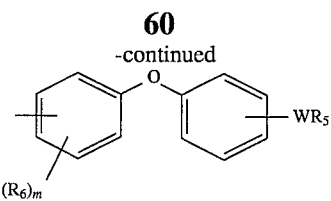

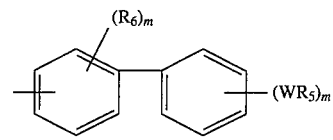

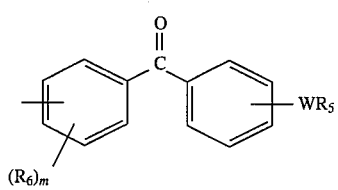

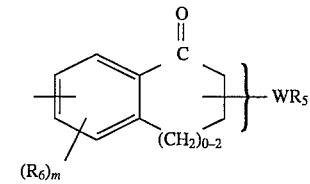

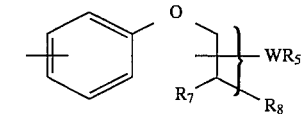

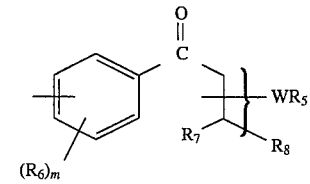

and n, at each occurrence is from 1–4 and m, at each occurrence, ranges from 0–2.

4. The compounds of claim 2 wherein:

W is a bond, —(CH$_2$)$_n$— or —O—(CH$_2$)$_n$—;

R$_5$ is —CO$_2$H;

R', R", and R''' are all —H;

R$_6$ is, at each occurrence, selected individually from H, halo, or C$_1$-C$_4$ alkyl; and R$_4$ is:

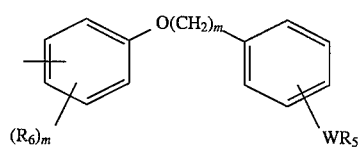

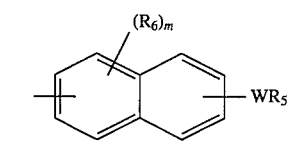

-continued

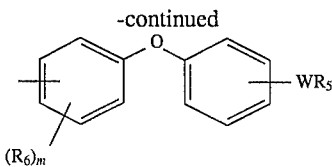

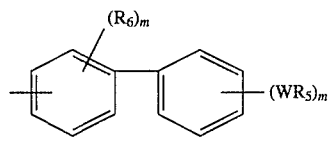

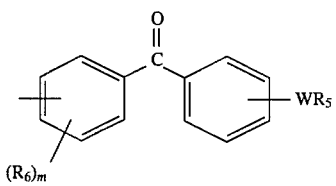

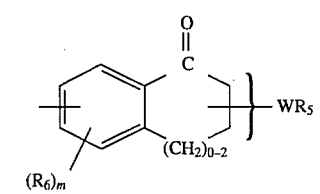

and

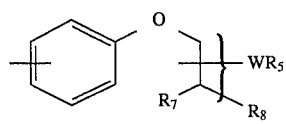

wherein
m ranges from 0–1, n ranges from 1–4; and $R_7$ and $R_8$ are both either H or —$CH_3$.

5. A pharmaceutical formulation comprising:

| Compound | Wt. % |
| --- | --- |
| a) A compound of Claim 1 | 0.1%–99.9 wt % |
| b) Fillers, inerts, carriers, excipients, solvents, lubricants, or mixtures thereof | Remainder |

6. A pharmaceutical formulation comprising:

| | |
| --- | --- |
| a) A compound of Claim 2 | 0.1%–99.9 wt % |
| b) Fillers, inerts, carriers, excipients, solvents, lubricants, or mixtures thereof | Remainder |

7. A pharmaceutical formulation comprising:

| | |
| --- | --- |
| a) A compound of Claim 3 | 0.1%–99.9 wt % |
| b) Fillers, inerts, carriers, excipients, solvents, lubricants, or mixtures thereof | Remainder |

8. A pharmaceutical formulation comprising:

| | |
| --- | --- |
| a) A compound of Claim 4 | 0.1%–99.9 wt % |
| b) Fillers, inerts, carriers, excipients, solvents, lubricants, or mixtures thereof | Remainder |

9. A compound of claim 1, or its pharmaceutically acceptable salts, having the formula;

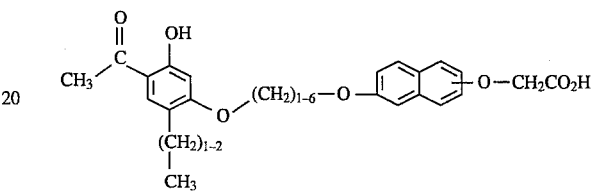

10. A compound of claim 1, or its pharmaceutically acceptable salts, having the formula:

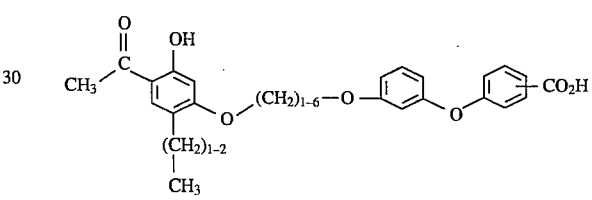

11. A compound of claim 1 having the formula:

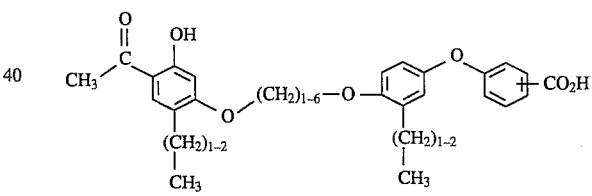

12. A compound of claim 1, or its pharmaceutically acceptable salts, having the formula:

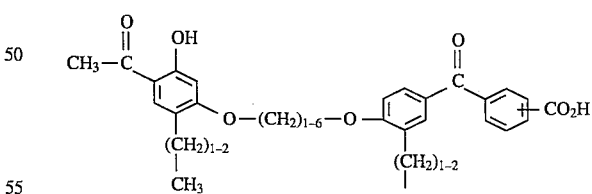

13. A method of treating a mammal suffering from a disease state characterized by the presence of an excess of leukotriene, $LTB_4$, which method comprises administering to said mammal an effective amount of one or more compounds of claim 1.

14. The method of claim 13 wherein the effective amount of compound(s) ranges from about 0.1 mg/Kg body weight to about 200 mg/Kg body weight of the mammal.

* * * * *